United States Patent [19]

Emonds-Alt et al.

[11] Patent Number: 5,712,288
[45] Date of Patent: *Jan. 27, 1998

[54] QUATERNARY BASIC AMIDES, METHOD OF PREPARING THEM AND PHARMACEUTICAL COMPOSITIONS IN WHICH THEY ARE PRESENT

[75] Inventors: Xavier Emonds-Alt, Combaillaux; Patrick Gueule, Teyran; Vincenzo Proietto, Saint Georges d'Orques; Didier Van Broeck, Murviel les Montpellier, all of France

[73] Assignee: Sanofi, Paris, France

[ * ] Notice: The term of this patent shall not extend beyond the expiration date of Pat. No. 5,583,134.

[21] Appl. No.: 734,029

[22] Filed: Oct. 18, 1996

Related U.S. Application Data

[60] Division of Ser. No. 239,417, May 6, 1994, Pat. No. 5,583,134, which is a continuation-in-part of Ser. No. 129,311, Sep. 30, 1993, abandoned.

[30] Foreign Application Priority Data

Sep. 30, 1992 [FR] France ................... 92 12083

[51] Int. Cl.⁶ .................... A61K 31/44; C07D 453/02
[52] U.S. Cl. .................... 514/305; 546/133
[58] Field of Search ................ 514/305; 546/133

[56] References Cited

U.S. PATENT DOCUMENTS

| | | | |
|---|---|---|---|
| 4,916,156 | 4/1990 | Mosse et al. | 514/510 |
| 5,236,921 | 8/1993 | Emonds-alt et al. | 514/252 |
| 5,317,020 | 5/1994 | Emonds-Alt et al. | 514/255 |
| 5,340,822 | 8/1994 | Emonds-Alt et al. | 514/316 |
| 5,411,971 | 5/1995 | Emonds-Alt et al. | 514/318 |
| 5,554,763 | 9/1996 | Emonds-Alt et al. | 548/453 |
| 5,567,700 | 10/1996 | Miller et al. | 514/226.8 |
| 5,583,134 | 12/1996 | Emonds-Alt et al. | 514/212 |

*Primary Examiner*—Alan L. Rotman
*Assistant Examiner*—Garth M. Dahlen
*Attorney, Agent, or Firm*—Bacon & Thomas

[57] ABSTRACT

The invention relates to quaternary basic amides of the formula

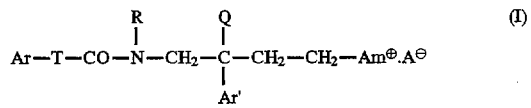

in which

Ar is an optionally substituted mono-, di- or tri-cyclic aromatic or heteroaromatic group;

T is a direct bond, a hydroxymethylene group, an alkoxymethylene group in which the alkoxy group is $C_1$–$C_4$, or a $C_1$–$C_5$-alkylene group;

Ar' is an unsubstituted or mono- or poly-substituted phenyl, a thienyl, a benzothienyl, a naphthyl or an indolyl;

R is hydrogen or a $C_1$–$C_4$-alkyl, or a $C_1$–$C_4$-ω-alkoxy ($C_2$–$C_4$)alkyl, or a $C_2$–$C_4$-ω-alkanoyloxy ($C_1$–$C_4$) alkyl;

Q is hydrogen;

or else Q and R together form a 1,2-ethylene, 1,3-propylene or 1,4-butylene group;

$Am^{\oplus}$ is the radical

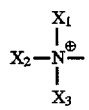

in which $X_1$, $X_2$ and $X_3$, together with the nitrogen atom to which they are bonded, form a 1-azoniabicyclo[2.2.2]octane optionally substituted by a phenyl or benzyl group; and $A^{\ominus}$ is a pharmaceutically acceptable anion.

These compounds are useful for the preparation of drugs intended for the treatment of pathological conditions involving the tachykinin system.

19 Claims, No Drawings

QUATERNARY BASIC AMIDES, METHOD OF PREPARING THEM AND PHARMACEUTICAL COMPOSITIONS IN WHICH THEY ARE PRESENT

The present application is a continuation-in-part of U.S. application Ser. No. 08/239,417, filed May 6, 1994, now U.S. Pat. No. 5,583,134, which is a continuation-in-part of U.S. application Ser. No. 08/129,311, filed Sep. 30, 1993, now abandoned.

The present invention relates to novel quaternary basic amides, to a method of preparing them and to the pharmaceutical compositions in which they are present as active principles.

More particularly, the present invention relates to a novel class of quaternary basic amides for therapeutic use in pathological phenomena involving the tachykinin system, such as: pain (D. Regoli et al., Life Sciences, 1987, 40, 109–117), allergy and inflammation (J. E. Morlay et al., Life Sciences, 1987, 41, 527–544), circulatory insufficiency (J. Losay et al., 1977, Substance P, Von Euler, U.S. and Pernow ed., 287–293, Raven Press, New York), gastrointestinal disorders (D. Regoli et al., Trends Pharmacol. Sci., 1985, 6, 481–484) and respiratory disorders (J. Mizrahi et al., Pharmacology, 1982, 25, 39–50), these examples being neither limiting nor exclusive.

Ligands endogenous to the tachykinin receptors have been described, such as substance P (SP), neurokinin A ($NK_A$) (S. J. Bailey et al., 1983, Substance P, P. Skrabanck ed., 16–17 Boole Press, Dublin) and neurokinin B ($NK_B$) (S. P. Watson, Life Sciences, 1983, 25, 797–808).

Thus, according to one of its features, the present invention relates to quaternary basic amides of the formula

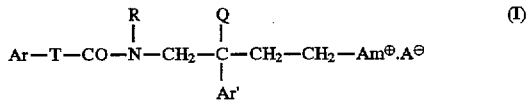

in which

Ar is an optionally substituted mono-, di- or tri-cyclic aromatic or heteroaromatic group;

T is a direct bond, a hydroxymethylene group, an alkoxymethylene group in which the alkoxy group is $C_1$–$C_4$, or a $C_1$–$C_5$-alkylene group;

Ar' is a phenyl which is unsubstituted or mono- or poly-substituted by a substituent selected from: a halogen atom, preferably a chlorine or fluorine atom, a trifluoromethyl, a $C_1$–$C_4$-alkoxy or a $C_1$–$C_4$-alkyl, said substituents being identical or different, a thienyl, a benzothienyl, a naphthyl or an indolyl;

R is hydrogen or a $C_1$–$C_4$-alkyl, or a $\omega$-($C_1$–$C_4$) alkoxy ($C_2$–$C_4$)alkyl, or a $\omega$-($C_2$–$C_4$)alkanoyloxy ($C_1$–$C_4$) alkyl;

Q is hydrogen;

or else Q and R together form a 1,2-ethylene, 1,3-propylene or 1,4-butylene group;

$Am^{\oplus}$ is the radical

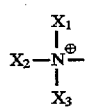

in which $X_1$, $X_2$ and $X_3$, together with the nitrogen atom to which they are bonded, form an azabicyclic or azatricyclic system optionally substituted by a phenyl or benzyl group; and $A'$ is a pharmaceutically acceptable anion.

The pharmaceutically acceptable anions are those normally used to salify the quaternary ammonium ions of products for pharmaceutical use, preferably chloride, bromide, iodide, hydrogensulfate, methanesulfonate, paratoluenesulfonate, acetate and benzenesulfonate ions.

In particular, in formula (I), Ar is a mono-, di- or tri-cyclic aromatic or heteroaromatic group which can carry one or more substituents and in which a carbon atom of the aromatic carbocycle or aromatic heterocycle is directly bonded to T.

More particularly, the radical Ar can be a phenyl group which may be unsubstituted or may optionally contain one or more substituents.

If Ar is a phenyl group, this can preferably be mono- or di-substituted, especially in the 2,4-position but also for example in the 2,3-, 4,5-, 3,4- or 3,5-position; it can also be trisubstituted, especially in the 2,4,6-position but also for example in the 2,3,4-, 2,3,5-, 2,4,5- or 3,4,5-position, tetrasubstituted, for example in the 2,3,4,5-position, or pentasubstituted. The substituents of the phenyl group can be: F; Cl; Br; I; CN; OH; $NH_2$; NH—$CONH_2$; $NO_2$; $CONH_2$; $CF_3$; $C_1$–$C_{10}$-alkyl, preferably $C_1$–$C_4$-alkyl, methyl or ethyl being preferred, as well as, for example, n-propyl, isopropyl, n-butyl, isobutyl, sec-butyl, tert-butyl, pentyl or n-pentyl, hexyl or n-hexyl, octyl or n-octyl, nonyl or n-nonyl or decyl or n-decyl; alkenyl containing 2 to 10 carbon atoms, preferably 2–4 carbon atoms, for example vinyl, allyl, prop-1-enyl, isopropenyl, butenyl or but-1-en-1-, -2-, -3- or -4-yl, but-2-en-1-yl, but-2-en-2-yl, pentenyl, hexenyl or decenyl; alkynyl containing 2 to 10 carbon atoms, preferably 2–4 carbon atoms, for example ethynyl, prop-1-yn-1-yl, propargyl, butynyl or but-2-yn-1-yl, pentynyl or decynyl; cycloalkyl containing 3 to 8 carbon atoms, preferably 5 or 6 carbon atoms, cyclopentyl or cyclohexyl being preferred, as well as, for example, cyclopropyl, cyclobutyl, 1-, 2- or 3-methylcyclopentyl, 1-, 2-, 3- or 4-methylcyclohexyl, cycloheptyl or cyclooctyl; bicycloalkyl containing 4 to 11 carbon atoms, preferably 7 carbon atoms, exo- or endo-2-norbornyl being preferred, as well as, for example, 2-isobornyl or 5-camphyl; hydroxyalkyl containing 1 to 5 carbon atoms, preferably 1–2 carbon atoms, hydroxymethyl and 1- or 2-hydroxyethyl being preferred, as well as, for example, 1-hydroxyprop-1-yl, 2-hydroxyprop-1-yl, 3-hydroxyprop-1-yl, 1-hydroxyprop-2-yl, 1-hydroxybut-1-yl or 1-hydroxypent-1-yl; alkoxy containing 1 to 10 carbon atoms, preferably 1–4 carbon atoms, isopropoxy or ethoxy being preferred, as well as, for example, n-propoxy, methoxy, n-butoxy, isobutoxy, sec-butoxy, tert-butoxy, pentoxy, hexyloxy, heptyloxy, octyloxy, nonyloxy or decyloxy; alkoxyalkyl containing 2 to 10 carbon atoms, preferably from 2 to 6 carbon atoms, for example alkoxymethyl or alkoxyethyl, such as methoxymethyl or 1- or 2-methoxyethyl, 1- or 2-n-butoxyethyl or 1- or 2-n-octyloxyethyl; alkoxyalkoxyalkyl containing up to 10 carbon atoms, preferably from 4 to 7 carbon atoms, for example alkoxyalkoxymethyl such as 2-methoxyethoxymethyl, 2-ethoxyethoxymethyl or 2-isopropoxyethoxymethyl, or alkoxyalkoxyethyl such as 2-(2-methoxyethoxy)ethyl or 2-(2-ethoxyethoxy)ethyl; alkoxyalkoxy containing from 2 to 10 carbon atoms, preferably from 3 to 6 carbon atoms, for example 2-methoxyethoxy, 2-ethoxyethoxy or 2-n-butoxyethoxy; alkenyloxy containing 2 to 10 carbon atoms, preferably 2 to 4 carbon atoms, allyloxy being preferred, as well as, for example, vinyloxy, propenyloxy, isopropenyloxy, butenyloxy such as but-1-en-1-, -2-, -3- or -4-yloxy, but-2-en-1-yloxy or but-2-en-2-yloxy, pentenyloxy, hexenyloxy or decenyloxy; alkenyloxyalkyl having up to 10 carbon atoms, preferably 3–6 carbon atoms, for example allyloxymethyl; alkynyloxy containing from 2 to 10 carbon atoms, preferably 2 to 4 carbon atoms, propargyloxy being preferred, as well as, for example, ethynyloxy, prop-1-yn-1-yloxy, butynyloxy or but-2-yn-1-yloxy, pentynyloxy or decynyloxy; alkynyloxyalkyl containing from 3 to 10 carbon atoms, preferably 3 to 6 carbon atoms, for example ethynyloxymethyl, propargyloxymethyl or 2-(but-2-yn-1-yloxy)ethyl; cycloalkoxy containing 3 to 8 carbon atoms, preferably 5 or 6 carbon atoms, cyclopentoxy or cyclohexyloxy being preferred, as well as, for example, cyclopropoxy, cyclobutoxy, 1-, 2- or 3-methylcyclopentoxy, 1-, 2-, 3- or 4-methylcyclohexyloxy, cycloheptyloxy or cyclooctyloxy; alkylthio containing from 1 to 10 carbon atoms, preferably 1 to 4 carbon atoms, methylthio or ethylthio being preferred, as well as, for example, n-propylthio, isopropylthio, n-butylthio, isobutylthio, sec-butylthio, tert-butylthio, pentylthio, hexylthio, octylthio, nonylthio or decylthio; alkylthioalkyl containing from 2 to 10 carbon atoms, preferably 2 to 6 carbon atoms, for example methylthiomethyl, 2-methylthioethyl or 2-n-butylthioethyl; acylamino, namely alkanoylamino containing from 1 to 7 carbon atoms, preferably 1 to 4 carbon atoms, formylamino and acetylamino being preferred, as well as propionylamino, butyrylamino, isobutyrylamino, valerylamino, caproylamino or heptanoylamino, or aroylamino or benzylamino; acylaminoalkyl, preferably alkanoylaminoalkyl containing from 2 to 8 carbon atoms, preferably 3 to 6 carbon atoms, such as formylaminoethyl, acetylaminoethyl, propionylaminoethyl, n-butyrylaminoethyl, formylaminopropyl, acetylaminopropyl, propionylaminopropyl, formylaminobutyl or acetylaminobutyl, as well as propionylaminobutyl or butyrylaminobutyl; acyloxy containing from 1 to 6 carbon atoms, preferably 2 to 4 carbon atoms, acetoxy, propionyloxy or butyryloxy being preferred, as well as, for example, formyloxy, valeryloxy or caproyloxy; alkoxycarbonyl containing from 2 to 5 carbon atoms, preferably 2 or 3 carbon atoms, methoxycarbonyl and ethoxycarbonyl being preferred, as well as, for example, n-propoxycarbonyl, isopropoxycarbonyl, n-butoxycarbonyl, isobutoxycarbonyl, sec-butoxycarbonyl or tert-butoxycarbonyl; cycloalkoxycarbonyl containing from 4 to 8 carbon atoms, preferably 6 or 7 carbon atoms, cyclopentoxycarbonyl and cyclohexyloxycarbonyl being preferred, as well as cyclopropoxycarbonyl, cyclobutoxycarbonyl or cycloheptyloxycarbonyl; alkylaminocarbonylamino containing from 2 to 4 carbon atoms, such as methylaminocarbonylamino, ethylaminocarbonylamino or propylaminocarbonylamino; dialkylaminocarbonylamino containing from 3 to 7 carbon atoms, preferably 3 to 5 carbon atoms, dimethylaminocarbonylamino being preferred, as well as di-n-propylaminocarbonylamino or diisopropylaminocarbonylamino; (pyrrolidin-1-yl)carbonylamino; cycloalkylaminocarbonylamino containing from 4 to 8 carbon atoms, preferably 6 or 7 carbon atoms, cyclopentylaminocarbonylamino and cyclohexylaminocarbonylamino being preferred, as well as cyclopropylaminocarbonylamino, cyclobutylaminocarbonylamino or cycloheptylaminocarbonylamino; alkylaminocarbonylaminoalkyl containing from 3 to 9 carbon atoms, preferably 4 to 7 carbon atoms, methylaminocarbonylaminoethyl, ethylaminocarbonylaminoethyl, ethylaminocarbonylaminopropyl and ethylaminocarbonylaminobutyl being preferred, as well as, for example, methylaminocarbonylaminomethyl, n-propylaminocarbonylaminobutyl and n-butylaminocarbonylaminobutyl; dialkylaminocarbonylaminoalkyl containing from 4 to 11 carbon atoms, for example dimethylaminocarbonylaminomethyl, diethylaminocarbonylaminoethyl, diethylaminocarbonylaminopropyl and diethylaminocarbonylaminobutyl; (pyrrolidin-1-yl)carbonylaminoethyl; (piperidin-1-yl)carbonylaminoethyl; cycloalkylaminocarbonylaminoalkyl containing from 5 to 12 carbon atoms, preferably 8 to 11 carbon atoms, cyclopentylaminocarbonylaminoethyl, cyclopentylaminocarbonylaminopropyl, cyclopentylaminocarbonylaminobutyl, cyclohexylaminocarbonylaminoethyl, cyclohexylaminocarbonylaminopropyl and cyclohexylaminocarbonylaminobutyl being preferred, as well as, for example, cyclopropylaminocarbonylaminoethyl or cycloheptylaminocarbonylaminoethyl; alkoxycarbonylaminoalkyl containing from 3 to 12 carbon atoms, preferably 4 to 9 carbon atoms, methoxycarbonylaminoethyl, ethoxycarbonylaminoethyl, n-propoxycarbonylaminoethyl, isopropoxycarbonylaminoethyl, n-butoxycarbonylaminoethyl, isobutoxycarbonylaminoethyl, sec-butoxycarbonylaminoethyl, tert-butoxycarbonylaminoethyl, ethoxycarbonylaminopropyl, n-butoxycarbonylaminopropyl, ethoxycarbonylaminobutyl and n-butoxycarbonylaminobutyl being preferred, as well as, for example, n-propoxycarbonylaminopropyl, n-propoxycarbonylaminobutyl or isopropoxycarbonylaminobutyl; cycloalkoxycarbonylaminoalkyl containing from 5 to 12 carbon atoms, preferably 8 to 11 carbon atoms, cyclopentoxycarbonylaminoethyl, cyclopentoxycarbonylaminopropyl, cyclopentoxycarbonylaminobutyl, cyclohexyloxycarbonylaminoethyl, cyclohexyloxycarbonylaminopropyl and cyclohexyloxycarbonylaminobutyl being preferred, as well as, for example, cyclopropoxycarbonylaminomethyl or cycloheptyloxycarbonylaminoethyl; carbamoylalkyl containing from 2 to 5 carbon atoms, preferably 2 carbon atoms, carbamoylmethyl being preferred, as well as carbamoylethyl, carbamoylpropyl or carbamoylbutyl; alkylaminocarbenylalkyl containing from 3 to 9 carbon atoms, preferably 3 to 6 carbon atoms, methylaminocarbonylethyl, ethylaminocarbonylmethyl, n-propylaminocarbonylmethyl, isopropylaminocarbonylmethyl, n-butylaminocarbonylmethyl, isobutylaminocarbonylmethyl, sec-butylaminocarbonylmethyl and tert-butylaminocarbonylmethyl being preferred, as well as, for example, ethylaminocarbonylethyl, ethylaminocarbonylpropyl, ethylaminocarbonylbutyl, propylaminocarbonylbutyl or n-butylaminocarbonylbutyl; dialkylaminocarbonylalkyl containing from 4 to 11 carbon atoms, preferably 4 to 8 carbon atoms, dimethylaminocarbonylmethyl, diethylaminocarbonylmethyl and di-n-propylaminocarbonylmethyl being preferred, as well as, for example, diethylaminocarbonylethyl, diethylaminocarbonylpropyl or diethylaminocarbonylbutyl; (pyrrolidin-1-yl)carbonylmethyl; (piperidin-1-yl)carbonylmethyl; (piperidin-1-yl)carbonylethyl; cycloalkylaminocarbonylalkyl containing from 5 to 12 carbon atoms, preferably 7 or 8 carbon atoms, cyclopentylaminocarbonylmethyl and cyclohexylaminocarbonylmethyl being preferred, as well as, for example, cyclopropylaminocarbonylmethyl, cyclobutylaminocarbonylmethyl, cycloheptylaminomethyl, cyclohexylaminocarbonylethyl, cyclohexylaminocarbonylpropyl or cyclohexylaminocarbonylbutyl; alkylaminocarbonylalkoxy containing from 3 to 10 carbon atoms, preferably 3 to 5 carbon atoms, methylaminocarbonylmethoxy being preferred, as well as, for example, methylaminocarbonylethoxy or methylaminocarbonylpropoxy; dialkylaminocarbonylalkoxy containing from 4 to 10 carbon atoms, preferably 4 to 7 carbon atoms, such as dimethylaminocarbonylmethoxy or diethylaminocarbonylethoxy; (piperidin-1-yl)carbonylmethoxy; and cycloalkylaminocarbonylalkoxy containing from 5 to 11 carbon atoms, preferably 7 or 8 carbon atoms, such as cyclopentylaminocarbonylmethoxy or cyclohexylaminocarbonylmethoxy.

The radical Ar can also be a bicyclic aromatic group such as 1- or 2-naphthyl or 1-, 2-, 3-, 4-, 5-, 6- or 7-indenyl, in which one or more bonds can be hydrogenated, it being possible for said groups to be unsubstituted or optionally to contain one or more substituents such as: a halogen, more particularly a fluorine atom, and alkyl, phenyl, cyano, hydroxyalkyl, hydroxy, $C_1$–$C_4$-alkoxy, oxo, alkylcarbonylamino, alkoxycarbonyl and thioalkyl groups in which the alkyls are $C_1$–$C_4$.

The radical Ar can also be a pyridyl, thiadiazolyl, indolyl, indazolyl, imidazolyl, benzimidazolyl, quinolyl, benzotriazolyl, benzofuranyl, benzothienyl, benzothiazolyl, benzisothiazolyl, isoquinolyl, benzoxazolyl, benzoxazinyl, benzodioxinyl, isoxazolyl, benzopyranyl, thiazolyl, thienyl, furyl, pyranyl, chromenyl, isobenzofuranyl, pyrrolyl, pyrazolyl, pyrazinyl, pyrimidinyl, pyridazinyl, indolizinyl, phthalazinyl, quinazolinyl, acridinyl, isothiazolyl, isochromanyl or chromanyl group in which one or more double bonds can be hydrogenated, it being possible for said groups to be unsubstituted or optionally to contain one or more substituents such as: alkyl, phenyl, cyano, hydroxyalkyl, hydroxy, alkylcarbonylamino, alkoxycarbonyl and thioalkyl groups in which the alkyls are $C_1$–$C_4$.

Advantageously, the radical Ar is a phenyl which is unsubstituted or mono- or poly-substituted by a halogen atom, more particularly a chlorine or fluorine atom, a trifluoromethyl, a $C_1$–$C_4$-alkyl, a hydroxy or a $C_1$–$C_4$-alkoxy, a naphthyl which is unsubstituted or mono- or poly-substituted by a halogen, a trifluoromethyl, a $C_1$–$C_4$-alkyl, a hydroxy or a $C_1$–$C_4$-alkoxy, a pyridyl, a thienyl, an indolyl, a quinolyl, a benzothienyl or an imidazolyl.

The radical

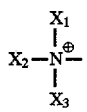

represented by the substituent $Am^\oplus$ in formula (I) is preferably the residue of an azabicyclic or azatricyclic system selected from:

(a) 1-azoniabicyclo[2.2.0]hexane
(b) 1-azoniabicyclo[3.1.0]hexane
(c) 1-azoniabicyclo[2.2.1]heptane
(d) 1-azoniabicyclo[2.2.2]octane
(e) 1-azoniabicyclo[3.2.1]octane
(f) 1-azoniabicyclo[3.2.2]nonane
(g) 1-azoniabicyclo[3.3.1]nonane
(h) hexahydro-1H-pyrrolizinium-4
(i) octahydroindolizinium-4
(j) octahydro-2H-quinolizinium-5
(k) 1-azoniatricyclo[3.3.1.1$^{3,7}$]decane
(l) 4-phenyl-1-azoniabicyclo[2.2.2]octane, the groups (d) and (l) being particularly preferred.

Particularly preferred quaternary basic amides according to the present invention are those of formula (I) in which simultaneously:

Ar is a 3-isopropoxyphenyl group;

T is a methylene group;

R and Q are respectively methyl and hydrogen; 2-acetoxyethyl and hydrogen; or R and Q form together a 1,3-propylene group;

Ar' is 3,4-dichlorophenyl;

$Am^\oplus$ is a radical (d) or (l) as defined above; and $A^-$ is a pharmaceutically acceptable anion, preferably chloride, methanesulfonate or benzenesulfonate. These products, of the formula

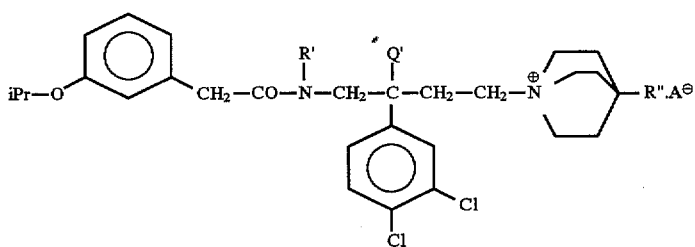

The particularly preferred compounds are those of formula (I) in which Ar is a phenyl group substituted by an isopropoxy group, advantageously in the 3-position.

In formula (I), T is preferably a methylene group.

The substituents R and Q are preferably respectively, methyl and hydrogen; 2-methoxyethyl and hydrogen; 2-acetoxyethyl and hydrogen; or R and Q form together a 1,3-propylene group.

The substituent Ar' is preferably a phenyl group advantageously substituted by two chlorine atoms, more particularly in the 3- and 4-positions.

The radical represented by $Am^\oplus$ preferably contains from 5 to 9 carbon atoms in the azabicyclic or azatricyclic system.

in which iPr is isopropyl, R' and Q' are respectively methyl and hydrogen; 2-acetoxyethyl and hydrogen; or R' and Q' form together a 1,3-propylene group, R" is hydrogen or a phenyl group and $A^-$ is as defined above, especially the methanesulfonate or chloride ion, are potent substance P antagonists.

The compounds of formula (I') in which R' and Q' together form a 1,3-propylene group are extremely potent and show a greater affinity for the neurokinin-1 receptor than does substance P itself. They therefore constitute the preferred feature of the present invention.

Among these compounds, those of formula (I"):

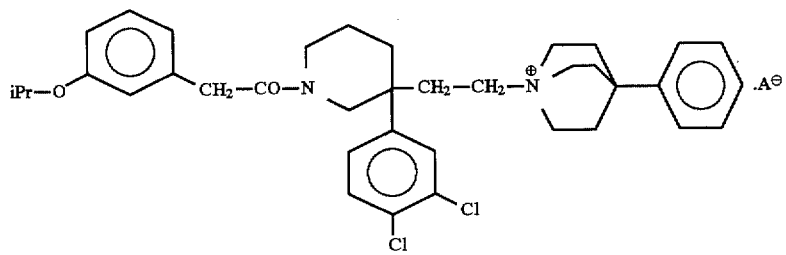

(I'')

in which $A^\ominus$ is a pharmaceutically acceptable anion, especially methanesulfonate, chloride and benzenesulfonate, are the most valuable.

According to another feature, the present invention relates to a method of preparing the compounds of formula (I) above, which comprises treating a derivative of the formula $$Ar-T-CO-N(R)-CH_2-C(Ar')(Q)-CH_2-CH_2-O-Y \quad (II)$$

in which Y is any removable group, preferably a methanesulfonyl or benzenesulfonyl group with a cyclic tertiary amine of the formula $$X_2-N(X_1)(X_3) \quad (III)$$

in which $X_1$, $X_2$ and $X_3$, together with the nitrogen atom to which they are bonded, form an azabicyclic or azatricyclic system optionally substituted by a phenyl or benzyl group, in an organic solvent, at a temperature between room temperature and 120° C., and isolating the resulting product, or else, if appropriate, exchanging the methanesulfonate anion of the resulting quaternary salt with another pharmaceutically acceptable anion.

The organic solvent used is preferably a polar aprotic solvent, for example acetonitrile, N,N-dimethylformamide or N,N-dimethylphenylacetamide, but it is also possible to use an ether, for example tetrahydrofuran, dioxane or methyl t-butyl ether, or a ketone, for example methyl ethyl ketone, acetonitrile being particularly preferred.

In the temperature range indicated above, the preferred temperature is 70°–90° C. If acetonitrile is used as the solvent, the reaction is advantageously carried out at the reflux point of the reaction mixture.

The product obtained in this way is isolated by the usual techniques, for example by concentration of the solvents, then washing of the residue with water and then purification by the conventional techniques, for example by chromatography or recrystallization.

The methanesulfonate anion resulting from the reaction between the tertiary amine of formula (III) and the methanesulfonyloxy derivative of formula (II) can be exchanged, in situ or after isolation of the compound (I) in which $A^\ominus$ is the methanesulfonate ion, with another anion $A^\ominus$ by the conventional methods, for example by exchange in a solution such as a solution of hydrochloric acid in the case where $A^\ominus$ is a chloride anion, or by exchange of the anion with another anion by elution of the compound (I) on an ion exchange resin, for example Amberlite IRA68® or Duolite A375®.

The derivatives of formula (II) used as starting compounds for the method of the present invention can be prepared according to Scheme 1 below, where, in the formulae indicated:

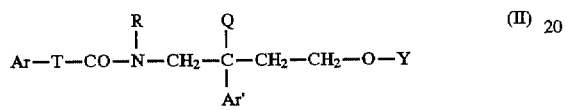

for Route A : Q = H; R = H, $C_1$–$C_4$-alkyl

for Route B : R + Q = —$(CH_2)_n$—, where n = 2, 3, 4

In Scheme 1, the reactions in the various steps are shown in a representative way so as to indicate the type of said reactions without giving the means employed, which are known.

Thus, for example, in Route A, step 2, and in Route B, step 6, "$H_2$" means that the starting nitrile is subjected to reduction, for example to catalytic hydrogenation (Raney Ni in ethanol, in the presence of ammonia, to give the primary amine IV).

In the same step 2 of Route A, the term "alkylation" means that, after reduction, the primary amine is subjected to an alkylation reaction which is either direct with an alkyl halide or sulfate, or indirect by means of acylation and reduction of the carbonyl group. Thus, for example, reaction of the primary amine (IV) with ethyl chloroformate and reduction of the ethoxycarbonyl group gives the product of formula (IV) in which R is methyl, as described in EP-0 428 434 and EP-0 474 561. The compound of formula (IV) in which R is $C_2$–$C_4$-alkyl is prepared by replacing the ethyl chloroformate with the chloride (or other functional derivative) of a $C_2$–$C_4$-alkanoic acid and by reducing the carbonyl group of the resulting N-acylated derivative. Replacing ethyl chloroformate with ethyl ethyloxalyle, ethyl hemimalonate or ethyl hemisuccinate, for example, gives the corresponding N-acyl derivatives. The carbonyl groups are then reduced according to the conventional methods to obtain the ω-hydroxy($C_2$–$C_4$)alkyl derivatives which are O-acylated or O-alkylated in order to obtain the ω-alkanoyloxyalkyl derivatives or the ω-alkoxyalkyl derivatives of formula IV in which R is ω-($C_2$–$C_4$)alkanoyloxy($C_2$–$C_4$)alkyl or ω-($C_1$–$C_4$)alkoxy($C_2$–$C_4$)alkyl. Likewise, replacing alkyl chloroformates with the chloride of an ω-($C_1$–$C_4$) alkoxy($C_2$–$C_4$)alkanoic acid, followed by reduction as described above, directly gives the ω-alkoxyalkyl derivatives of formula IV in which R is ω-($C_1$–$C_4$)alkoxy($C_2$–$C_4$)alkyl.

Also, for example, in step 4 of Route A, "$H^+$" means that the tetrahydropyranyloxy group is subjected to acid hydrolysis under the conditions well known in the literature.

SCHEME 1

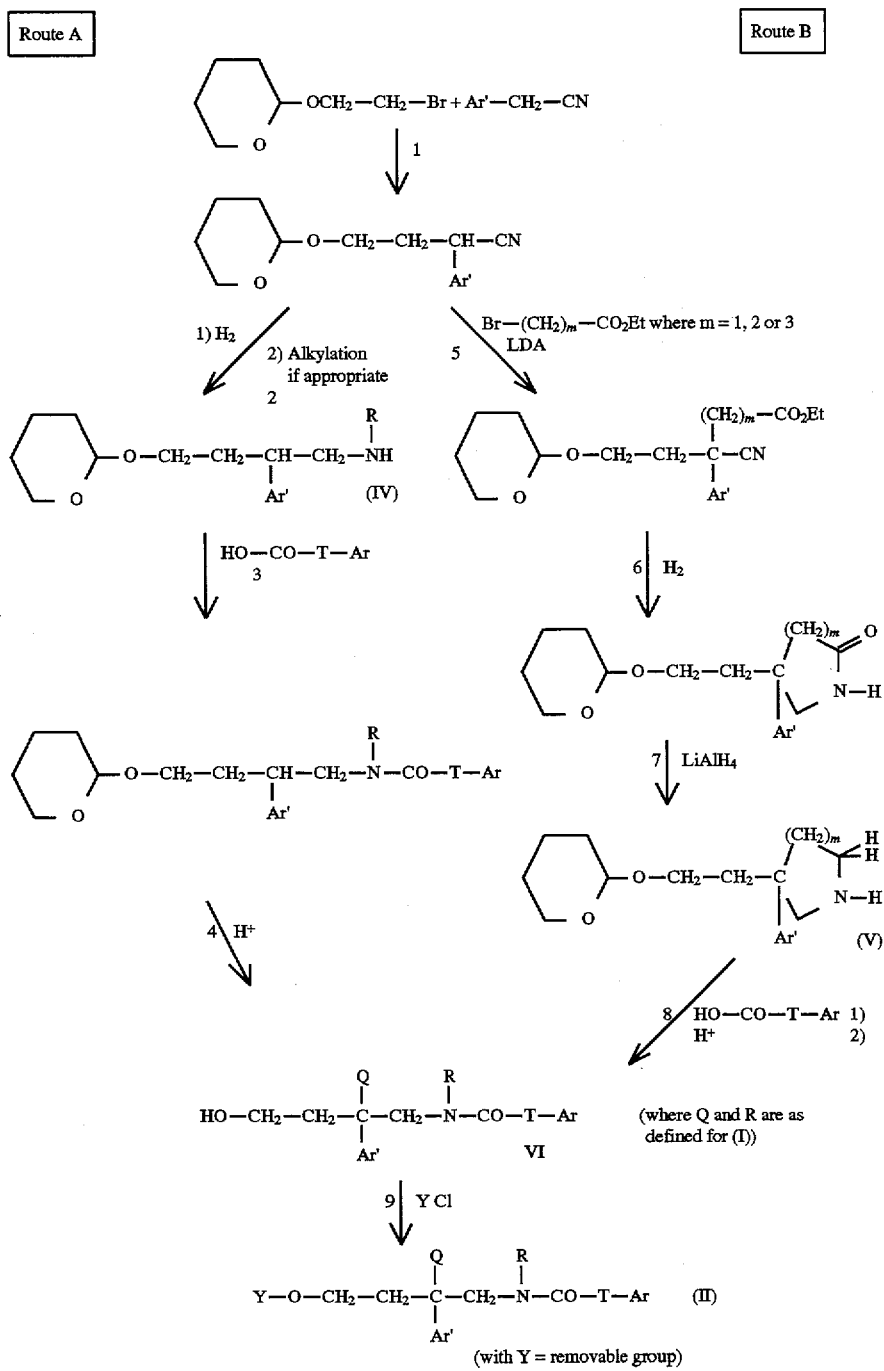

The meaning of the substituent Ar depends on the choice of acid HO—CO—T—Ar used in steps 3 and 8 in the form of one of its functional derivatives. All these acids are well known in the literature, readily prepared according to the literature or commercially available.

The meaning of the substituent Ar' depends on the choice of nitrile Ar'—CH₂—CN, which, on reaction with 2-tetrahydropyranyloxy-1-bromoethane, hydrogenation of the resulting product and N-alkylation if appropriate (step 2), gives the amine.

Route A of Scheme 1 in which R=H, alkyl and Q=H is described in the literature and in patent applications EP-A-0 428 434 and EP-A-0 474 561.

Route B of Scheme 1 involves a series of reactions well known to those skilled in the art, such as the alkylation of a nitrile with a brominated derivative in the presence of lithium diisopropylamide (LDA) (step 5), followed by reduction of the nitrile in the presence of a catalyst to give the corresponding amine after reduction of the intermediate amide (step 7) obtained during the cyclization (step 6), for example according to A. V. El'tsov et al., Biol. Soedin., Akad. Nauk SSSR, 1965, 109–12 (CA, 1965, 63, 16299).

In both the routes of Scheme 1, the reaction conditions of certain steps are the same. Thus the reduction of step 2 (Route A) and step 6 (Route B) is carried out under the same conditions. Likewise, step 7 (Route B) and the reduction of the N-acylated derivative or the ethoxycarbonyl in the indirect alkylation reaction of step 2 (Route B) take place under the same conditions. Finally, the acylation in step 3 (Route A) and step 8 (Route B) is carried out under the same conditions.

The method of preparing the compounds (I) according to the invention consists in reacting the derivative (II), prepared by reacting the alcohol (IV) with a YCl derivative, for example mesyl chloride or benzenesulfonyl chloride (step 9), with a tertiary amine of formula (III) in accordance with Scheme 2 below.

SCHEME 2

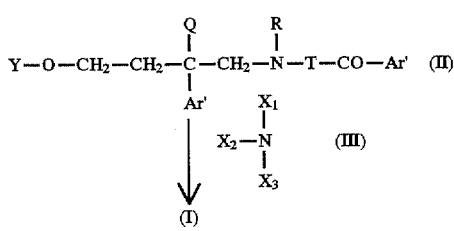

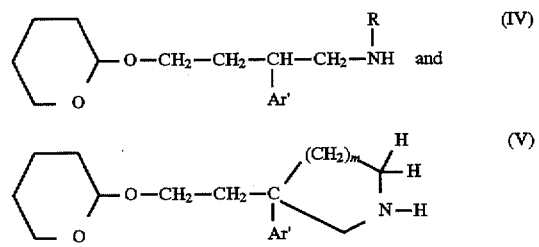

in which Ar' and R are as defined for (I) and m is 1, 2 or 3.

The enantiomers are then separated by conventional methods such as crystallization or chiral preparative high pressure chromatography.

The preparation of the optically pure compounds is illustrated in Scheme 3 below, where "*" means that the carbon atom identified by this symbol has the defined configuration (+) or (−).

In Scheme 3, the last step is indicated as being performed with the free acid, but it can be carried out with a functional derivative thereof, which could attack the molecule on both the hydroxy group and the amino group. In this case, it is desirable to protect the hydroxy group again, for example with dihydropyran to form the tetrahydropyranyl ether.

The preparation of the compounds (VI*) according to Scheme 3 in which R is hydrogen or a $C_1$–$C_4$-alkyl group and Q is hydrogen is described in EP-A-0 428 434 and EP-A-0 474 561.

SCHEME 3

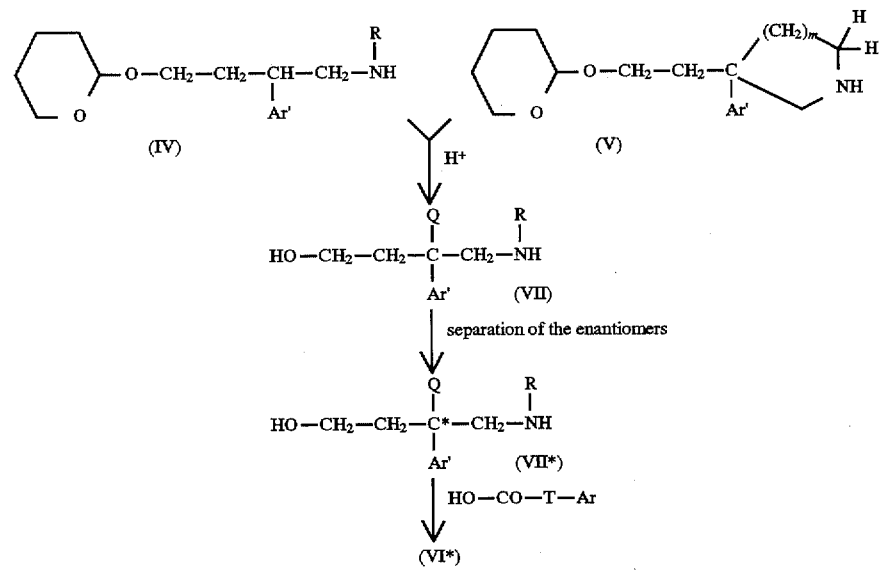

Resolution of the racemic mixtures (I) makes it possible to isolate the enantiomers (I*), which also form part of the invention.

It is preferable, however, to resolve the racemates at the stage of the intermediate amino alcohols, which are capable of giving salts with optically active acids. The amino alcohols correspond to the compounds (IV) and (V) obtained according to step 2 (Route A) and according to step 7 (Route B) of Scheme 1 after deprotection of the compounds by hydrolysis in an acid medium:

The optically pure compounds of formula (VI*) in which Q and R are bonded together to form 1,2-ethylene, 1,3-propylene or 1,4-butylene are prepared in the same manner.

In particular, the compound (VII*) obtained after separation of the enantiomers of (VII) is coupled with an acid of the formula Ar—T—COOH, in the presence of a coupling agent, by the usual methods. As indicated above, it is possible to use a functional derivative of this acid, such as the acid itself appropriately activated by cyclohexylcarbodiimide or by benzotriazolyl-N-oxytrisdimethylaminophosphonium hexafluorophosphate (BOP), for example, or else one of the functional derivatives which react with amines, for example an anhydride, a mixed anhydride, the acid chloride or an activated ester such as the paranitrophenyl ester.

The resulting compound of the formula

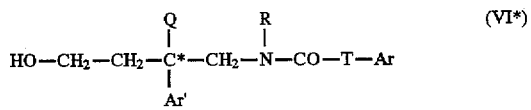

is then reacted with a YCl derivative according to step 9 of Scheme 1 to give the optically pure derivative (II).

The products of formula (I) in which T is a hydroxymethylene, $C_1$-$C_4$-alkoxymethylene or $C_2$-$C_5$-alkylidene group possess two centers of asymmetry. In this case, the diastereoisomers and the pure isomers can be prepared by reacting the optically pure amino alcohol and either the optically pure or the racemic acid HO—CO—T—Ar; in the latter case, the diastereoisomers can be separated for example by chromatography.

The reaction with the tertiary amine (III) makes it possible to prepare the product (I) according to the invention in optically pure form.

The amines of formula (III) are those described in the literature.

Among these amines, those which are preferred contain from 5 to 9 carbon atoms in the ring system and a nitrogen atom, examples being cited below:

(a') 1-azabicyclo[2.2.0]hexane prepared according to C. A. Grob et al., Helv. Chim. Acta, 1964, (47), 8, 2145–55.

(b') 1-azabicyclo[3.1.0]hexane prepared according to A. L. Logothetis, J. Am. Chem. Soc., 1965, (87), 4, 749–754.

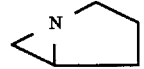

(c') 1-azabicyclo[2.2.1]heptane prepared according to Gassman et al., J. Am. Chem. Soc., 1968, (90), 5, 1355–6.

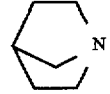

(d') 1-azabicyclo[2.2.2]octane or quinuclidine.

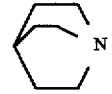

(e') 1-azabicyclo[3.2.1]octane prepared according to B. Thill et al., J. Org. Chem., 1968, (33), 12, 4376–80.

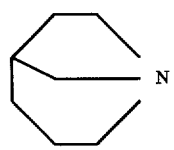

(f') 1-azabicyclo[3.2.2]nonane prepared according to C. Ruggles et al., J. Am. Chem. Soc., 1988, (110), 17, 5692–8.

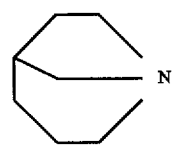

(g') 1-azabicyclo[3.3.1]nonane prepared according to S. Miyano et al., J. Chem. Soc., Perkin Trans. 1, 1988, 5, 1057–63.

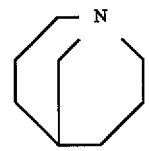

(h') hexahydro-1H-pyrrolizine-4 prepared according to P. Edwards et al., Tetrahedron Letters, 1984, (25), 9, 939–42.

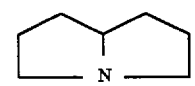

(i') octahydroindolizine-4 prepared according to J. Chastanet et al., J. Org. Chem., 1985, (50), 16, 2910–14.

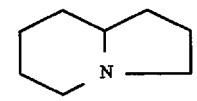

(j') octahydro-2H-quinolizine-5 prepared according to P. Edwards et al., Tetrahedron Letters, 1984, (25), 9, 939–42.

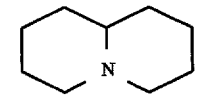

(k') 1-azatricyclo[3.3.1.1$^{3,7}$]decane or 1-azaadamantane prepared according to Y. Bubnov et al., J. Organomet. Chem., 1991, 412, (1–2), 1–8.

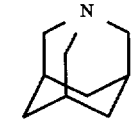

(1') 4-phenyl-1-azabicyclo[2.2.2]octane or 4-phenylquinuclidine prepared according to T. Perrine, J. Org. Chem., 1957, 22, 1484–1489.

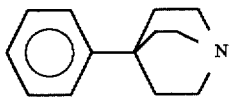

The compounds of formula (I) above also include those in which one or more hydrogen or carbon atoms have been replaced with their radioactive isotope, for example tritium or carbon-14. Such labeled compounds are useful in research, metabolic or pharmacokinetic work and in biochemical tests as receptor ligands.

The compounds according to the invention were subjected to biochemical tests.

The compounds (I) showed antagonistic properties towards the binding of substance P in tests performed on rat cortex membranes and IM9 lymphoblastic cells according to M. A. Cascieri et al., J. Biol. Chem., 1983, 258, 5158–5164, and D. D. Paya et al., J. Immunol., 1984, 133, 3260–3265.

Among the compounds tested, (+)-1-[2-[3-(3,4-dichlorophenyl)-1-[(3-isopropoxyphenyl)acetyl]piperidin-3-yl]ethyl]-4-phenyl-1-azoniabicyclo[2.2.2]octane chloride (compound 4) proved to be a potent antagonist of the NK1 receptor of substance P: it inhibits the binding of substance P to its receptor with an inhibition constant (Ki) of 10–20 pM in the various biochemical tests performed.

In particular, the compounds of the present invention are active principles of pharmaceutical compositions, whose toxicity is compatible with their use as drugs.

The compounds of formula (I) above can be used in daily doses of 0.01 to 100 mg per kilogram of body weight of the mammal to be treated, preferably in daily doses of 0.1 to 50 mg/kg. In humans, the dose can preferably vary from 0.5 to 4000 mg per day, more particularly from 2.5 to 1000 mg per day, depending on the age of the subject to be treated or the type of treatment: prophylactic or curative.

For their use as drugs, the compounds of formula (I) are generally administered in dosage units. Said dosage units are preferably formulated as pharmaceutical compositions in which the active principle is mixed with a pharmaceutical excipient.

Thus, according to another feature, the present invention relates to pharmaceutical compositions in which a compound of formula (I) is present as the active principle.

In the pharmaceutical compositions of the present invention for oral, sublingual, subcutaneous, intramuscular, intravenous, transdermal, local or rectal administration, the active principles can be administered to animals and humans in unit forms of administration, mixed with conventional pharmaceutical carriers. The appropriate unit forms of administration include oral forms such as tablets, gelatin capsules, powders, granules and solutions or suspensions to be taken orally, sublingual and buccal forms of administration, subcutaneous, intramuscular, intravenous, intranasal or intraocular forms of administration and rectal forms of administration.

When a solid composition in the form of tablets is prepared, the main active principle is mixed with a pharmaceutical vehicle such as gelatin, starch, lactose, magnesium stearate, talc, gum arabic or the like. The tablets can be coated with sucrose or other appropriate substances or else they can be treated so as to have a prolonged or delayed activity and so as to release a predetermined amount of active principle continuously.

A preparation in the form of gelatin capsules is obtained by mixing the active principle with a diluent and pouring the mixture obtained into soft or hard gelatin capsules.

A preparation in the form of a syrup or elixir can contain the active principle together with a sweetener, which is preferably calorie-free, methylparaben and propylparaben as antiseptics, a flavoring and an appropriate color.

The water-dispersible granules or powders can contain the active principle mixed with dispersants or wetting agents or with suspending agents such as polyvinylpyrrolidone, as well as with sweeteners or taste correctors.

Rectal administration is effected using suppositories, which are prepared with binders melting at the rectal temperature, for example cacao butter or polyethylene glycols.

Parenteral, intranasal or intraocular administration is effected using aqueous suspensions, isotonic saline solutions or sterile and injectable solutions which contain pharmacologically compatible dispersants and/or wetting agents, for example propylene glycol or butylene glycol.

Administration by inhalation is effected using an aerosol which contains for example sorbitan trioleate or oleic acid, as well as trichlorofluoromethane, dichlorofluoromethane, dichlorotetrafluoroethane or any other biologically compatible propellant gas.

The active principle can also be formulated as microcapsules, with one or more carriers or additives if appropriate.

In each dosage unit, the active principle of formula (I) is present in the amounts appropriate to the daily doses envisaged. In general, each dosage unit is suitably adjusted according to the dosage and the intended type of administration, for example tablets, gelatin capsules and the like, sachets, ampoules, syrups and the like, and drops, so that such a dosage unit contains from 0.5 to 1000 mg of active principle, preferably from 2.5 to 250 mg, to be administered one to four times a day.

According to another feature, the present invention relates to the use of the products of formula (I) for the preparation of drugs intended for the treatment of physiological disorders associated with an excess of tachykinins, especially substance P, and all the tachykinin-dependent pathologies of the respiratory, gastrointestinal, urinary, immune or cardiovascular system and of the central nervous system as well as pain and migraine.

For example without however implying a limitation:
sharp and chronic pains induced for example by migraine, by the pains of the cancer and angina patient, by chronic inflammatory processes such as osteoarthritis and rheumatoid arthritis, inflammations such as obstruent chronic respiratory diseases, asthma, allergies, rhinites, over-sensitiveness such as pollen or acarida over-sensitiveness, rheumatoid arthrites, osteoarthrites, psoriasis, ulcerative colites, Crohn's disease, inflammation of the intestines (irritable colon), prostatitis, neurological bladder, cystitis, urethritis, nephritis, complaints of the immune system induced by the deletion or the stimulation of the functions of the immune cells for example rheumatoid arthritis, psoriasis, Crohn's disease, diabetes, lupus, complaints of the central nervous system such as anxiety, depression, psychotic states, schizophrenia, mania, dementia, epilepsy, Parkinson's disease, Alzheimer's disease, drug-dependency, Down's syndrome and Huntington's chorea as well as the neurodegenerative diseases, complaints of the gastrointestinal system such as nausea, irritable colon, gastric and duodenal ulcers, diarrheas, hypersecretions, complaints of the cardiovascular system such as the vascular aspects of migraine, oedemas, thrombosis, angina and vascular spasms.

The present invention also includes a method of treating said complaints at the doses indicated above.

The Examples which follow illustrate the invention without however implying a limitation.

The melting points of the products, m.p., were measured on a Koffler heating bench.

PREPARATIONS

A. AMINO ALCOHOLS (VII) and (VII*)
PREPARATION I: Scheme 1—Route A (a) α-(2-Tetrahydropyranyloxyethyl)-3,4-dichlorobenzeneacetonitrile 16.5 g of an 80% dispersion of sodium hydride in oil are suspended in 200 ml of dry tetrahydrofuran. A solution of 100 g of 3,4-dichlorophenylacetonitrile in 500 ml of tetrahydrofuran is added dropwise at 20° C. over 30 minutes and the reaction mixture is then stirred at room temperature for 2 hours. The mixture is cooled to −20° C., a solution of 118 g of 1-bromo-2-tetrahydropyranyloxyethane in 100 ml of tetrahydrofuran is added, the mixture is allowed to warm up to room temperature and, after 2 hours, a solution of 50 g of ammonium chloride in 3 liters of water is added. Extraction is carried out with 1.5 liters of ether and the extract is washed with a saturated solution of NaCl, decanted, dried over $MgSO_4$ and concentrated under vacuum. The residue is chromatographed on silica gel using $CH_2Cl_2$ and then ethyl acetate (95/5 v/v) as the eluent. The pure product fractions are concentrated under vacuum to give 118 g of an oil.

(b) 2-(2-Tetrahydropyranyloxyethyl)-3,4-dichlorobenzeneethanamine 118 g of the nitrile obtained above are dissolved in 700 ml of absolute ethanol. 300 ml of concentrated aqueous ammonia are added, after which Raney nickel (10% of the amount of starting nitrile) is added while sweeping with nitrogen. Hydrogenation is then carried out under a hydrogen atmosphere at room temperature and ordinary pressure. 16 liters are absorbed in 4 hours. The catalyst is filtered off on Célite, the filtrate is concentrated under vacuum and the residue is taken up in a saturated solution of NaCl. After extraction with ether and drying over $MgSO_4$, 112 g of an oil are obtained.

(c) 2-(2-Hydroxyethyl)-3,4-dichlorobenzeneethanamine 81 g of the product obtained above according to (b) are dissolved in 38 ml of methanol. 80 ml of a saturated solution of hydrogen chloride in ether are added, the temperature being kept between 20° and 25° C. The mixture is stirred for 30 minutes at room temperature and then concentrated to dryness. The residue is dissolved in 250 ml of water, washed twice with ethyl ether, rendered alkaline with a solution of NaOH and extracted with $CH_2Cl_2$. After drying over $MgSO_4$, the extract is concentrated to dryness, the residue is taken up in 800 ml of isopropyl ether, an insoluble material is filtered off on Célite, the filtrate is concentrated under vacuum to about 300 ml and seeded with crystals of amino alcohol and the mixture is stirred overnight. The crystals are filtered off and rinsed with isopropyl ether and then with n-pentane to give 30.2 g of the expected product. M.p. =90°–91° C.

(d) 2-(2-Hydroxyethyl)-3,4-dichlorobenzeneethanamine (+)

A solution of 44.7 g of the product obtained according to step (c) above in 300 ml of methanol is added to a boiling solution of 29 g of D(−)-tartaric acid in 800 ml of methanol. The mixture is allowed to cool to room temperature and stirred for 4 hours. The product is filtered off and rinsed with ethanol and then ether to give 34.1 g of tartrate. This is recrystallized from 1.75 l of methanol to give 26.6 g of tartrate.

$[\alpha]_D^{25}$=−4.2° (c=1, in $H_2O$)

The tartrate is taken up in 120 ml of water, rendered alkaline with a solution of NaOH and extracted twice with $CH_2Cl_2$ and the extract is dried over $MgSO_4$ and concentrated to dryness. The residue is taken up in a small quantity of isopropyl ether, n-pentane is added and the mixture is filtered to give 15.4 g of product. M.p.=79°–80° C.

$[\alpha]_D^{25}$=+9.4° (c=1, in $CH_3OH$)

(e) N-Methyl-2-(2-hydroxyethyl)-3,4-dichlorobenzeneethanamine (+) hydrochloride (e1) Ethyl N-[4-(2-hydroxyethyl)-2-(3,4-dichlorophenyl)butyl]carbamate 15 g of the product obtained according to step (d) above are dissolved in 200 ml of $CH_2Cl_2$. 9.9 ml of triethylamine are added. The mixture is cooled to 0° C. and a solution of 6.3 ml of ethyl chloroformate in 30 ml of $CH_2Cl_2$ is added dropwise at this temperature. After 15 minutes, the mixture is washed with water, then with a dilute solution of HCl and then with a saturated aqueous solution of $NaHCO_3$. After drying over $MgSO_4$, it is concentrated to dryness to give 20 g of product in the form of an oil.

(e2) Reduction of the ethoxycarbonyl group to a methyl group

A solution of 20 g of the product obtained according to step (e1) above in 150 ml of anhydrous THF is added to 5.1 g of a suspension of lithium aluminum hydride in 60 ml of anhydrous THF. The mixture is refluxed for 1 hour. It is hydrolyzed with 20 ml of water, the inorganic material is filtered off and the filtrate is concentrated to dryness. The oil obtained is dissolved in 100 ml of acetone. A saturated solution of hydrogen chloride in ether is added until the pH is 1, after which ether is added until turbidity appears. The mixture is stirred for 1 hour and the crystals are filtered off and rinsed with a small quantity of acetone and then with ether to give 11 g of N-methyl-2-(2-hydroxyethyl)-3,4-dichlorobenzeneethanamine hydrochloride. M.p.=129° C.

$[\alpha]_D^{25}$ =+8.4° (c=1, in $CH_3OH$)

(f) N-Methyl-2-(2-hydroxyethyl)-3,4-dichlorobenzeneethanamine (−) hydrochloride

The (−) enantiomer is obtained by following the above procedure starting from L(+)-tartaric acid. M.p.=129° C.

$[\alpha]_D^{20}$=−8.4° (c=1, in $CH_3OH$)

PREPARATION II: Scheme 1—Route B, m=1

(a) 3,4-Dichloro-α-(2-tetrahydropyranyloxyethyl)benzeneacetonitrile 20 g of a 55–60% dispersion of sodium hydride in oil are suspended in 200 ml of dry tetrahydrofuran. A solution of 85 g of 3,4-dichlorophenylacetonitrile in 500 ml of tetrahydrofuran is added dropwise at 20° C. over 30 minutes and the reaction mixture is then stirred at room temperature for 2 hours. A solution of 98 g of 2-bromoethoxytetrahydropyran in 100 ml of tetrahydrofuran is added to the resulting mixture cooled to −20° C., the mixture is allowed to warm up to room temperature and, after 2 hours, a solution of 50 g of ammonium chloride in 3 liters of water is added. Extraction is carried out with 1.5 liters of ethyl ether and the extract is washed with a saturated solution of sodium chloride, decanted, dried over $MgSO_4$ and concentrated under vacuum. The residue is chromatographed on silica gel using dichloromethane as the eluent. The pure product fractions are concentrated under vacuum to give 83.6 g of an oil.

(b) Ethyl β-tetrahydropyranyloxyethyl-β-cyano-β-(3,4-dichlorophenyl)propionate 21 g of the nitrile prepared above according to (a) are dissolved in 100 ml of tetrahydrofuran, a solution of 0.067 mol of lithium diisopropylamide in 100 ml of tetrahydrofuran is then added dropwise at room temperature and the reaction mixture is stirred for one hour at room temperature. 12 g of ethyl bromoacetate are then added and the mixture is heated at 50° C. for two hours. The mixture is cooled, poured into a saturated solution of ammonium chloride and extracted with ethyl ether, the extract is washed with water and the ether phase is separated off by decantation, dried over $Na_2SO_4$ and concentrated under vacuum. The residue is purified by chromatography on silica gel using dichloromethane/ethyl acetate (100/1 v/v) as the eluent. Concentration of the pure fractions gives 13 g of the expected compound.

(c) 4-(2-Tetrahydropyranyloxyethyl)-4-(3,4-dichlorophenyl)-2-pyrrolidone 13 g of the compound prepared above are dissolved in 250 ml of ethanol and 40 ml of aqueous ammonia and are hydrogenated at room temperature and atmospheric pressure in the presence of Raney nickel. When the theoretical volume of hydrogen has been absorbed, the mixture is filtered on Célite and the filtrate is concentrated under vacuum. The residue is taken up in water and extracted with ethyl ether and the ether phase is then washed with water, dried over $MgSO_4$ and concentrated under vacuum to give 8.6 g of the expected product.

(d) 3-(2-Tetrahydropyranyloxyethyl)-3-(3,4-dichlorophenyl)pyrrolidine 3.9 g of the 4-(2-tetrahydropyranyloxyethyl)-4-(3,4-dichlorophenyl)-2-pyrrolidone prepared above are dissolved in 50 ml of tetrahydrofuran and the solution is added to a suspension of 0.9 g of lithium aluminum hydride in 5 ml of THF heated to 60° C. The reaction mixture is heated for one hour at 60° C. and then cooled. 1 ml of water, 1 ml of 4N sodium hydroxide and 3 ml of water are added. The inorganic material is filtered off and the filtrate is concentrated under vacuum. The residue is taken up in ethyl ether, dried over $MgSO_4$ and concentrated under vacuum to give 3.4 g of the expected product.

(e) 3-(2-Hydroxyethyl)-3-(3,4-dichlorophenyl)pyrrolidine

A solution of hydrogen chloride in ether is added to a solution of 3.4 g of 3-tetrahydropyranyloxyethyl-3-(3,4-dichlorophenyl)pyrrolidine in 20 ml of methanol until the pH is 1. The mixture is stirred for half an hour at room temperature and concentrated to dryness, the residue is taken up in water, rendered basic with a solution of sodium hydroxide and extracted with dichloromethane and the extract is washed with a saturated solution of NaCl, dried over $Na_2SO_4$ and evaporated to dryness to give an oil. This oil is taken up in 20 ml of an isopropyl ether/ether mixture (50/50 v/v). After stirring and filtration, the product is washed with ethyl ether and dried under vacuum over $P_2O_5$. 2.6 g of the expected product are isolated.

PREPARATION III: Scheme 1—Route B, m=2

(a) Ethyl γ-(2-tetrahydropyranyloxyethyl)-γ-cyano-γ-(3,4-dichlorophenyl)butanoate 21 g of the nitrile prepared according to step (a) above are dissolved in 100 ml of tetrahydrofuran, a solution of 0.067 mol of lithium diisopropylamide in 100 ml of tetrahydrofuran is then added dropwise at room temperature and the reaction mixture is stirred for one hour at room temperature. 12 g of ethyl bromopropionate are then added and the mixture is heated at 50° C. for two hours. The mixture is cooled, poured into a saturated solution of ammonium chloride and extracted with ether, the extract is washed with water and the ether phase is separated off by decantation, dried over $Na_2SO_4$ and concentrated under vacuum. The residue is purified by chromatography on silica gel using dichloromethane/ethyl acetate (100/1 v/v) as the eluent. Concentration of the pure fractions gives 13 g of the expected compound.

(b) 5-(2-Tetrahydropyranyloxyethyl)-5-(3,4-dichlorophenyl)-2-piperidinone 13 g of the compound prepared above are dissolved in 250 ml of ethanol and 40 ml of aqueous ammonia and are hydrogenated at room temperature and atmospheric pressure in the presence of Raney nickel. When the theoretical volume of hydrogen has been absorbed, the mixture is filtered on Célite and the filtrate is concentrated under vacuum. The residue is taken up in water and extracted with ether and the ether phase is then washed with water, dried over $MgSO_4$ and concentrated under vacuum to give 9 g of the expected product.

(c) 3-(2-Tetrahydropyranyloxyethyl)-3-(3,4-dichlorophenyl)piperidine 3.9 g of the 5-(2-tetrahydropyranyloxyethyl)-5-(3,4-dichlorophenyl)piperidinone prepared above are dissolved in 50 ml of tetrahydrofuran and the solution is added to a suspension of 0.9 g of lithium aluminum hydride in 5 ml of THF heated to 60° C. The reaction mixture is heated for one hour at 60° C. and then cooled. 1 ml of water, 1 ml of 4N sodium hydroxide and 3 ml of water are added. The insoluble portion is filtered off and the filtrate is concentrated under vacuum. The residue is taken up in ethyl ether, dried over $MgSO_4$ and concentrated under vacuum to give 3.4 g of the expected product.

(d) 3-(2-Hydroxyethyl)-3-(3,4-dichlorophenyl)piperidine

A saturated solution of hydrogen chloride in ether is added to a solution of 55 g of 3-(2-tetrahydropyranyloxyethyl)-3-(3,4-dichlorophenyl)piperidine in 200 ml of methanol until the pH is 1. The mixture is stirred for half an hour at room temperature and concentrated to dryness, the residue is taken up in water, rendered alkaline with a solution of NaOH and extracted with $CH_2Cl_2$ and the extract is washed with a saturated solution of NaCl, dried over $Na_2SO_4$ and evaporated to dryness to give an oil. This oil is taken up in 200 ml of an isopropyl ether/ether mixture (50/50 v/v). After stirring and filtration, the product is washed with ethyl ether and dried under vacuum over $P_2O_5$ to give 45 g of the expected product. M.p.=122° C.

(e) 3-(2-Hydroxyethyl)-3-(3,4-dichlorophenyl)piperidine (+)

A solution of 23.54 g of L(+)-tartaric acid in 750 ml of 100° ethanol is added to a refluxing solution of 43 g of the product obtained above in 250 ml of 100° ethanol. The reaction mixture is refluxed for half an hour and allowed to cool to room temperature and the crystals obtained are filtered off, washed with 100° ethanol and dried under vacuum at 50° C. over $P_2O_5$ to give 31 g of tartrate. After recrystallization from 540 ml of 100° ethanol and filtration, the tartrate is washed with ethyl ether and dried under vacuum over $P_2O_5$ to give 25 g of tartrate.

$[\alpha]_D^{20} = +8.5°$ (c=1, in $H_2O$)

The tartrate is then taken up in water, neutralized with a solution of NaOH and extracted with $CH_2Cl_2$ and the extract is washed with water, dried over $Na_2SO_4$ and evaporated to dryness. The oil is taken up in an ethyl ether/isopropyl ether mixture and the crystals are filtered off, washed with ethyl ether and dried under vacuum at 50° C. to give 13.5 g of base. M.p.=138° C.

$[\alpha]_D^{20}$ =+8.2° (c=1, in CH$_3$OH)

(f) 3-(2-Hydroxyethyl)-3-(3,4-dichlorophenyl)piperidine (−)

The (−) enantiomer is obtained by following the above procedure starting from D(−)-tartaric acid. M.p.=139° C.

$[\alpha]_D^{20}$=−8.4° (c=1, in CH$_3$OH)

PREPARATION IV: Scheme 1—Route B, m=3

(a) Ethyl δ-(2-tetrahydropyranyloxyethyl)-δ-cyano-δ-(3,4-dichlorophenyl)pentanoate 4.6 g of 60% NaH are added in small portions to a solution of 36 g of the above 3,4-dichloro-α-[(2-tetrahydropyranyloxy)ethyl]benzeneacetonitrile (prepared according to PREPARATION II (a)) in 100 ml of dimethylformamide. The reaction mixture is stirred for 3 hours at room temperature and cooled to 0° C. and 22.4 g of ethyl 4-bromobutyrate in 40 ml of dimethylformamide are then added. The reaction mixture is stirred for 3 hours at room temperature, poured into water and extracted with ether and the extract is washed with a saturated solution of NaCl, dried over Na$_2$SO$_4$ and concentrated under vacuum. The residue obtained is purified by chromatography on silica gel using toluene as the eluent to give 24 g of the expected product.

(b) 6-(2-Tetrahydropyranyloxyethyl)-6-(3,4-dichlorophenyl)perihydro-2-azepinone 8 g of the product obtained above, dissolved in 120 ml of ethanol, are hydrogenated at atmospheric pressure and room temperature in the presence of Raney nickel. When the theoretical volume of hydrogen has been consumed, the catalyst is filtered off and the filtrate is concentrated under vacuum. The oil obtained is then taken up in 20 ml of xylene and the reaction mixture is refluxed for 48 hours. It is evaporated and the residue obtained is purified by chromatography on silica gel using CH$_2$Cl$_2$/CH$_3$OH (100/1 v/v) as the eluent to give 4 g of the expected product in the form of an oil.

(c) 3-(2-Tetrahydropyranyloxyethyl)-3-(3,4-dichlorophenyl)perihydroazepine 1.7 g of the expected product are obtained in the form of an oil by following the previous preparation, step (d), starting from 2 g of the product obtained above and 0.49 g of lithium aluminum hydride.

(d) 3-(2-Hydroxyethyl)-3-(3,4-dichlorophenyl)perhydroazepine 1.3 g of the expected product are obtained by following the previous preparation, step (e), starting from 1.7 g of the product obtained above.

B. SUBSTITUTED PHENYLACETIC ACIDS 3-chlorophenylacetic acid and 3-ditrifluoromethylphenylacetic acid are commercially available.

B1. 3-ISOPROPOXYPHENYLACETIC ACID PREPARATION V. 1

3-Isopropoxyphenylacetic acid is not known in the literature but can be prepared by well-known methods of preparing alkoxyphenylacetic acids.

(a) Ethyl 3-hydroxyphenylacetate

A solution of 55 g of 3-hydroxyphenylacetic acid in 400 ml of 100° ethanol is refluxed overnight in the presence of a few drops of concentrated H2SO$_4$. It is evaporated to dryness and the residue is taken up in ethyl ether and washed with water and then with a saturated aqueous solution of NaHCO$_3$. After drying over MgSO$_4$ followed by evaporation, 58 g of an oil are obtained.

(b) Ethyl 3-isopropoxyphenylacetate

A solution of 58 g of the product obtained above, 88 g of K$_2$CO$_3$ and 108 g of 2-iodopropane in 300 ml of DMF is heated at 80°–100° C. for 8 hours. The DMF is evaporated off under vacuum and the residue is taken up in ethyl acetate and washed with a 10% aqueous solution of K$_2$CO$_3$. After drying over MgSO$_4$ followed by evaporation, the residue is purified by chromatography on silica gel using CH$_2$Cl$_2$ as the eluent to give 61 g of an oil.

(c) 3-Isopropoxyphenylacetic acid

A solution of 31 g of the product obtained above and 20 g of NaOH in 400 ml of ethanol is refluxed for 2 hours. It is evaporated to dryness and the residue is taken up in water and acidified with concentrated HCl. Extraction is carried out with ethyl ether and the extract is washed with water, dried over MgSO$_4$ and concentrated to dryness to give 27 g of the expected acid. M.p.=33°–35° C.

B2. 2-IODO-5-ISOPROPOXYPHENYLACETIC ACID PREPARATION V. 2

2-iodo-5-isopropoxyphenylacetic acid is not known in the literature but can be prepared by known methods for example according to R. E. Counsel et al., J. Med. Chem., 1973, 16, 6, 684–687 by replacing the benzyl chloride with the 2-iodopropane.

15 g of the thus prepared 2-iodo-5-isopropoxyphenylacetonitrile are dissolved in 160 ml of ethanol in the presence of 18 g of KOH and then the mixture is refluxed for two hours. It is concentrated under vacuum and the residue is taken up in water and successively it is washed with ethyl ether, the aqueous phase is acified by adding HCl until the pH is 1 and extracted with ethyl ether and the extract is washed with water, dried over Na$_2$SO$_4$ and filtered. It is concentrated under vacuum and the residue is purified by chromatography on silica gel using CH$_2$Cl$_2$—CH$_3$OH (100-2 v/v) as the eluent to give after concentration of the pure fractions, 8 g of the expected acid in the form of an oil. NMR Spectrum (200 MHz): 1.2 ppm—2CH$_3$; 3.5 ppm—1CH$_2$; 4.6 ppm—1CH; 6.6 ppm—1H aromatic; 6.9 ppm—1H aromatic; 7.6 ppm—1H aromatic.

C. ACYL DERIVATIVES (VI) AND SULFONYLOXY DERIVATIVES (II)

PREPARATION VI: Scheme 1—Route B, m=1

(a) 3-(2-Hydroxyethyl)-3-(3,4-dichlorophenyl)-1-(3-isopropoxyphenyl)acetylpyrrolidine 2.25 ml of triethylamine and then 2.6 g of the 3-(2-hydroxyethyl)-3-(3,4-dichlorophenyl)pyrrolidine prepared above are added to a solution of 1.9 g of 3-isopropoxyphenylacetic acid in 50 ml of CH$_2$Cl$_2$. The mixture is cooled to 0° C., 4.42 g of BOP are then added and the reaction mixture is allowed to warm up to room temperature. After 30 minutes, the mixture is concentrated under vacuum and the residue is taken up in ethyl ether and washed successively with water, a dilute solution of NaOH, a saturated solution of NaCl, a dilute solution of HCl, a saturated solution of NaCl and a solution of NaHCO$_3$. The ether phase is dried over MgSO$_4$, filtered and concentrated under vacuum to give 3.6 g of the expected product.

(b) 3-(2-Methanesulfonyloxyethyl)-3-(3,4-dichlorophenyl)-1-(3-isopropoxyphenyl)acetylpyrrolidine 2.2 g of the product prepared above are dissolved in 50 ml of CH$_2$Cl$_2$ and the solution is cooled to 0° C. 1.5 g of triethylamine are added and 0.57 g of methanesulfonyl chloride is then added dropwise. The reaction mixture is left to stand for 15 minutes at 0° C. and then concentrated under vacuum, the residue is taken up in ether and washed with water and the ether phase is dried over MgSO$_4$, filtered and concentrated under vacuum. The residue is chromatographed on silica gel using heptane/ethyl acetate (50/50 v/v) up to pure ethyl acetate as the eluent. The pure product fractions are concentrated under vacuum and the residue is then solidified in an ethyl ether/isopropyl ether mixture to give 2.5 g of the expected product.

PREPARATION VII: Scheme 1—Route B, m=2

(a) Optically pure 3-(2-hydroxyethyl)-3-(3,4-dichlorophenyl)-1-[(3-isopropoxyphenyl)acetyl]piperidine 22.5 ml of triethylamine and then 22 g of the 3-(2-hydroxyethyl)-3-(3,4-dichlorophenyl)piperidine (−) prepared above according to PREPARATION III (f) are added to a solution of 16 g of 3-isopropoxyphenylacetic acid in 500 ml of $CH_2Cl_2$. The mixture is cooled to 0° C., 42.6 g of BOP are then added and the reaction mixture is allowed to warm up to room temperature. After 30 minutes, the mixture is concentrated under vacuum and the residue is taken up in ether and washed successively with water, a dilute solution of NaOH, a saturated solution of NaCl, a dilute solution of HCl, a saturated solution of NaCl and a solution of $NaHCO_3$. The ether phase is dried over $MgSO_4$, filtered and concentrated under vacuum to give 36 g of optically pure product. (+)

(b) 3-(2-Methanesulfonyloxyethyl)-3-(3,4-dichlorophenyl)-1-[(3-isopropoxyphenyl)acetyl]piperidine 36 g of the product prepared above are dissolved in 500 ml of $CH_2Cl_2$ and the solution is cooled to 0° C. 11.5 ml of triethylamine are added and 6.3 ml of methanesulfonyl chloride are then added dropwise. The reaction mixture is left to stand for 15 minutes at 0° C. and then concentrated under vacuum, the residue is taken up in ether and washed with water and the ether phase is dried over $MgSO_4$, filtered and concentrated under vacuum. The residue is chromatographed on silica gel using heptane/ethyl acetate (50/50 v/v) up to pure ethyl acetate as the eluent. The pure product fractions are concentrated under vacuum and the residue is then solidified in an ethyl ether/isopropyl ether mixture to give 37.5 g of the expected product. M.p.=72° C.

$[\alpha]_D^{20} = +25.7°$ (c=1, in $CHCl_3$)

(c) 3-(2-Benzenesulfonyloxyethyl)-3-(3,4-dichlorophenyl)-1-[(3-isopropoxyphenyl)acetyl]piperidine 4.6 ml of triethylamine and then, dropwise, 4.3 ml of benzenesulfonyl chloride are added to 11.3 g of the product prepared above according to PREPARATION VII (a) in 160 ml of $CH_2Cl_2$ and the solution is cooled to 0° C. The reaction mixture is left to stand for 18 hours at room temperature and is then successively treated with 100 ml of HCl, 100 ml of 10% $Na_2CO_3$ and 100 ml of water. The organic phase is filtered off, dried over $Na_2SO_4$ and then concentrated under vacuum. The residue is chromatographed on silica gel using cyclohexane/AcOEt (80/20 v/v) as the eluent. The pure product fractions are concentrated to give 8.4 g of the expected product.

PREPARATION VIII: Scheme 1—Route B, m=3

(a) 3-(2-Hydroxyethyl)-3-(3,4-dichlorophenyl)-1-[(3-isopropoxyphenyl)acetyl]perihydroazepine 1.2 g of triethylamine and then 1.15 g of the 3-(2-hydroxyethyl)-3-(3,4-dichlorophenyl)azepine prepared above are added to a solution of 0.76 g of 3-isopropoxyphenylacetic acid in 50 ml of $CH_2Cl_2$. The mixture is cooled to 0° C., 1.77 g of BOP are then added and the reaction mixture is allowed to warm up to room temperature. After 30 minutes, the mixture is concentrated under vacuum and the residue is taken up in ethyl ether and washed successively with water, a dilute solution of NaOH, a saturated solution of NaCl, a dilute solution of HCl, a saturated solution of NaCl and a solution of $NaHCO_3$. The ether phase is dried over $MgSO_4$, filtered and concentrated under vacuum to give 1.8g.

(b) 3-(2-Methanesulfonyloxyethyl)-3-(3,4-dichlorophenyl)-1-[(3-isopropoxyphenyl)acetyl]perihydroazepine.

1.8 g of the product prepared above are dissolved in 50 ml of $CH_2Cl_2$ and the solution is cooled to 0° C. 0.38 g of triethylamine is added and 0.44 g of methanesulfonyl chloride is then added dropwise. The reaction mixture is left to stand for 15 minutes at 0° C. and then concentrated under vacuum, the residue is taken up in ethyl ether and washed with water and the ether phase is dried over $MgSO_4$, filtered and concentrated under vacuum. The residue is chromatographed on silica gel using heptane/ethyl acetate (50/50 v/v) up to pure ethyl acetate as the eluent.

The pure product fractions are concentrated under vacuum and the residue is then solidified in an ethyl ether/isopropyl ether mixture to give 2 g of the expected product.

D. AMINE (III)

PREPARATION IX: Scheme 2–4-benzylquinuclidine (a) 1-benzyl-4-carbamoylpiperidine.

100 g of isonipecotamide are placed in 550 ml of DMF and 127 g of potassium carbonate are added. 101 ml of benzyl bromide are then added dropwise while maintaining the temperature of the reaction mixture at 25° C. with an ice bath. The reaction mixture is left to stand one day at room temperature under stirring and then filtered, the precipitate is washed several times with DMF and then the organic phases are pooled and evaporated. The precipitate thus formed is extracted with $CH_2Cl_2$ and then washed with water. The organic phase is dried over $MgSO_4$ and evaporated under vacuum. After recrystallization from water, 101.51 g of the expected compound are recovered. M.p=163° C.

(b) 1-benzyl-4-cyanopiperidine.

100 g of the compound obtained in step (a) are dissolved in 334 ml of phosphoryl chloride, and the mixture is then refluxed during 2 hours. The reaction mixture is concentrated to dryness and 200 ml of toluene are added. The reaction mixture is again concentrated and poured into 1 l of water while maintaining the temperature at 25° C. with an ice bath, and the pH is raised to 10 by addition of 10N NaOH. The reaction mixture is extracted 3 times with $CH_2Cl_2$ and then dried over $MgSO_4$ and evaporated. The obtained liquid is purified by distillation under a pressure of 0.022 millibars at a temperature of 114°–116° C. 86.8 g of the expected compound are recovered.

(c) 1,4-dibenzyl-4-cyanopiperidine.

80 g of the compound obtained in step (b) are mixed with 650 ml of THF, and 295 ml of lithium diisopropylamide are added dropwise while the reaction mixture is maintained under nitrogen atmosphere and refrigerated at −50° C. After 1 h under stirring, 54 ml of benzyl bromide are added dropwise and then the temperature of the reaction mixture is allowed to rise to room temperature over 3 hours. The reaction mixture is then washed with 2 l of a mixture of ammonium chloride and ice. The product which precipitates is extracted with ether, and the organic phase is separated, dried over $MgSO_4$ evaporated to dryness, washed with pentane and filtered to give 106.8 g of the expected compound in the form of a white solid. M.p=92° C.

(d) 4-acetyl-1,4-dibenzylpiperidine chloride.

60 g of the compound obtained in step (c) are dissolved under stirring in 1 l of ether. 165 ml of methyllithium are added dropwise. After 3 hours under stirring, the reaction mixture is poured into 1 l of iced water. The organic phase is separated, dried over $MgSO_4$ and evaporated to dryness. The oil formed is refluxed for 2 hours with 1.3 l of 1M HCl and the reaction mixture is left to stand 24 hours at room temperature. The expected product crystallizes in the reaction mixture, and is then filtered, wrung, successively washed with acetone and ether and dried under vacuum at 120° C. to give 59.90 g of the expected compound. M.p= 240° C.

(e) 4-bromoacetyl-1,4-dibenzylpiperidine bromide.

58 g of the compound of step (d) are dissolved in 232 ml of acetic acid. 9.3 ml of bromine are added under stirring and the reaction mixture is maintained under stirring for 24 hours at room temperature. The expected product crystallizes in the reaction mixture and 300 ml of ether are added before filtering the formed compound. After washing with an acetone/ether mixture and then with ether and drying in a drying oven under vacuum, 70.6 g of the expected compound are recovered. M.p=200° C.

(f) 1,4-dibenzyl-3-oxoquinuclidinium bromide.

68 g of the compound of step (e) are suspended into 500 ml of water and the reaction mixture is rendered basic at pH>10 by addition of 10M NaOH. The formed product is extracted with ether, dried over MgSO₄ and then evaporated to dryness. The formed foam is taken up in 50 ml of acetone and stirred during 2 hours. The formed crystals are filtered and washed with ether to give 36.5 g of the expected compound. M.p=226° C.

(g) 4-benzyl-3-oxoquinuclidine.

35.5 g of the compound of step (f) are mixed with 3.6 g of 10 % Pd/C in 700 ml of methanol and the mixture is stirred under hydrogen atmosphere at atmospheric pressure. After absorption of 2.2 l of hydrogen, the catalyst is filtered off on Celite® and the solution is evaporated to dryness. The formed crystals are washed with ether and then dried. These crystals are dissolved in the minimum amount of water and the mixture is rendered basic by addition of 10N NaOH until all the amine precipitates. The amine is then filtered, rinsed with iced water and dried under vacuum to give 19.3 g of the expected product in the form of a white solid. M.p=110° C.

(h) 4-benzylquinuclidine.

16 g of the compound obtained in step (g) are added to 8 g of hydrazine hydrate and 14 g of KOH in 80 ml of triethyleneglycol. The reaction mixture is refluxed under nitrogen during 1 and a half hours. After distilling the water off, the reaction mixture is heated at 195° C. during 3 hours, poured into 1 l of iced water and extracted twice with ether. The ether phases are pooled, dried over MgSO₄ and evaporated to dryness. The formed solid is dissolved in the minimum amount of acetone and the mixture is rendered acid with chlorhydric ether until pH=1. The formed precipitate is washed several times with ether, filtered, dried, dissolved in the minimum amount of water, rendered basic until pH>10 and extracted twice with ether. The ether solution is dried over MgSO₄ and evaporated to give 10.4 g of the expected compound in the form of a white solid. M.p=49° C.

EXAMPLE 1

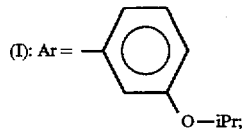

T = —CH₂—; R = —CH₃; Q = H;

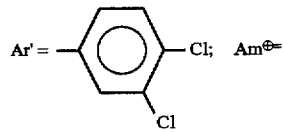

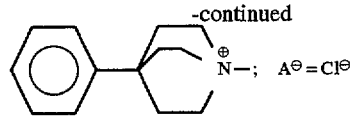

0.75 g of 4-phenylquinuclidine, synthesized according to T. Perrine, J. Org. Chem., 1957, 22, 1484–1489, and 1 g of N-[2-(3,4-dichlorophenyl)-4-methanesulfonyloxybutyl]-N-methyl-(3-isopropoxyphenyl)carboxamide, prepared according to EP-A-0 428 434, are dissolved in 5 ml of acetonitrile. The reaction mixture is refluxed for 4 hours and then concentrated under vacuum. The residue is taken up in CH₂Cl₂ and then washed successively with a 2N solution of HCl and a saturated solution of NaCl and the organic phase is dried over MgSO₄, filtered and concentrated under vacuum. The residue is solidified in ethyl ether to give 0.39 g of 1-[3-(3,4-dichlorophenyl)-4-(N-methyl-3-isopropoxyphenylacetylamino)butyl]-4-phenyl-1-azoniabicyclo[2.2.2]octane chloride (compound 1). M.p.= 98°–100° C.

EXAMPLE 2

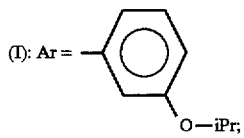

T = —CH₂—; R = —CH₃; Q = H;

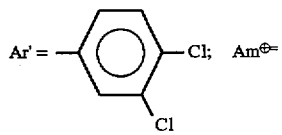

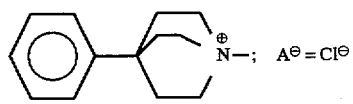

The optically pure derivative (−)-1-[3-(3,4-dichlorophenyl)-4-(N-methyl-3-isopropoxyphenylacetylamino)butyl]-4-phenyl-1-azoniabicyclo[2.2.2]octane chloride (compound 2), m.p.= 97°–99° C., is obtained by following the procedure of Example 1 using the optically pure derivative (−)-N-[2-(3,4-dichlorophenyl)-4-methanesulfonyloxybutyl]-N-methyl-(3-isopropoxyphenyl)carboxamide, prepared according to EP-A-0 428 434, as the starting material.

$[\alpha]_D^{20} = -47.2°$ (c=1, in CH₃OH)

EXAMPLE 3

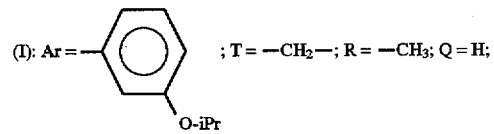

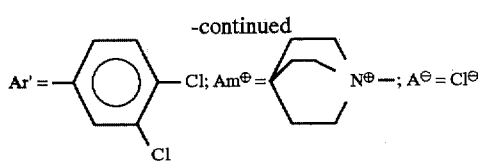

1-[3-(3,4-Dichlorophenyl)-4-(N-methyl-3-isopropoxyphenylacetylamino)butyl]-1-azoniabicyclo[2.2.2]-octane chloride (compound 3), m.p.=68°-70° C., is obtained by following the procedure of Example 1 using quinuclidine as the tertiary amine.

EXAMPLE 4

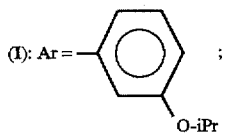

$T = -CH_2-$; $R + Q = -(CH_2)_3-$

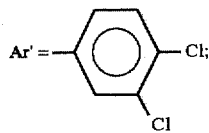

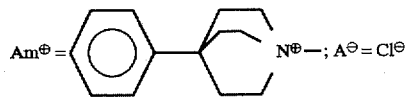

2.25 g of 4-phenylquinuclidine and 3.17 g of the mesylate prepared according to PREPARATION VII (b) are dissolved in 30 ml of acetonitrile and the reaction mixture is refluxed for 10 hours. The mixture is concentrated under vacuum and the residue is taken up in $CH_2Cl_2$ and washed successively with a 3N solution of HCl and then a saturated solution of NaCl. The organic phase is dried over $MgSO_4$, filtered and concentrated under vacuum. The residue precipitates from an acetone/ether mixture to give 2.8 g of optically pure (+)-1-[2-[3-(3,4-dichlorophenyl)-1-[(3-isopro-poxyphenyl)acetyl]piperidin-3-yl]ethyl]-4-phenyl-1-azoniabicyclo[2.2.2]octane chloride (compound 4). M.p.=132° C.

$[\alpha]_D^{20}=+16.3°$ (c=1, in $CH_3OH$)

EXAMPLE 5

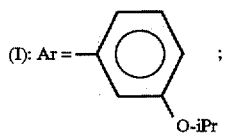

$T = -CH_2-$; $R + Q = -(CH_2)_3-$

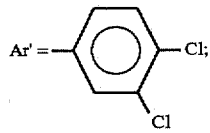

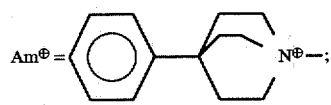

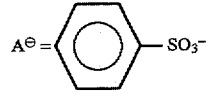

2.65 g of 4-phenylquinuclidine and 8.3 g of the benzenesulfonate prepared according to PREPARATION VII (c) are dissolved in 40 ml of acetonitrile and the reaction mixture is refluxed for 6 hours. The mixture is concentrated under vacuum and the residue is taken up in $CH_2Cl_2$ and washed successively with a 1% aqueous solution of benzenesulfonic acid and then with water. The organic phase is dried over $Na_2SO_4$, filtered and concentrated under vacuum. The residue precipitates from isopropyl ether to give 8 g of optically pure (+)-1-[2-[3-(3,4-dichlorophenyl)-1-[(3-isopropoxyphenyl)acetyl]piperidin-3-yl]ethyl]-4-phenyl-1-azoniabicyclo[2.2.2]octane benzenesulfonate (compound 5). M.p.=195.5° C.

$[\alpha]_D^{20}=-50.7°$ (c=1, in $CH_3OH$)

Compounds 6 to 12 described in TABLES I and II below are prepared by following

EXAMPLES 1 to 5.

TABLE I

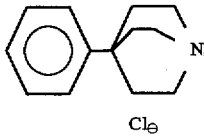

| Example n° | Ar' | R | T | Ar | M.p.; in °C. and/or [α]$_D$* |
|---|---|---|---|---|---|
| 6 | 3,4-diClC$_6$H$_3$ | CH$_3$ | — | 4-F-naphthyl | 150 −57.9° |
| 7 | 3,4-diFC$_6$H$_3$ | CH$_3$ | — | 4-F-naphthyl | 178 |
| 8 | 3,4-diFC$_6$H$_3$ | CH$_3$ | —CH$_2$— | 3-OiPr-C$_6$H$_4$ | 97 |
| 9 | naphthyl | H | — | 2,4-diOCH$_3$-C$_6$H$_3$ | 104–106 |

*The rotary powers, [α]$_D$, were measured at 20° C., c = 1 in CH$_3$OH.

TABLE II

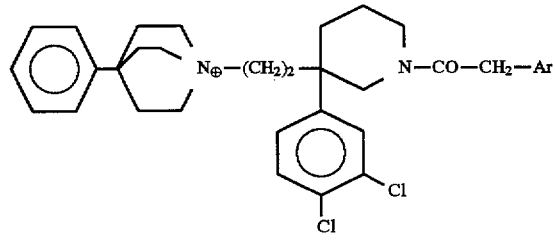

| Example n° | Ar | A$^\ominus$ | M.p.; °C. and/or [α]$_D$ |
|---|---|---|---|
| 10 | 3-OiPr-C$_6$H$_4$ | Cl$^\ominus$ | 125; −16.0° |
| 11 | 3-OH-C$_6$H$_4$ | Br$^\ominus$ | 196–198 |

TABLE II-continued

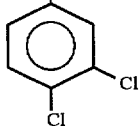

| Example n° | Ar | A$^\ominus$ | M.p.; °C. and/or [α]$_D$ |
|---|---|---|---|
| 12 | 3-I-4-OiPr-C$_6$H$_3$ | Cl$^\ominus$ | 156–160 +11.0° |

EXAMPLE 13

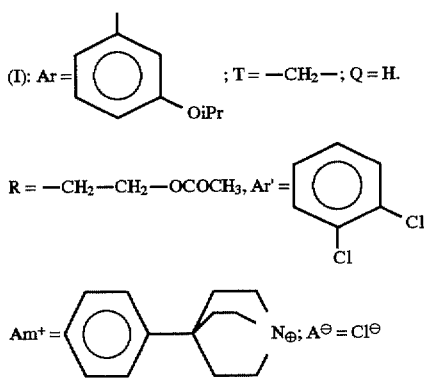

8.2 g of ethyloxalyl chloride are added dropwise to a solution of 19 g of 2-(2-tetrahydropyranyloxyethyl)-3,4-dichlorobenzeneethanamine (obtained according to PREPARATION (I)—Step (b)) and of 7 g of triethylamine. The reaction mixture is stirred for one hour at room temperature and concentrated under vacuum. The residue is taken up in ethyl ether and is successively washed with water, dried over $Na_2SO_4$ and concentrated under vacuum. The residue is chromatographed on silica gel using $CH_2Cl_2/CH_3OH$ (100/1 v/v) as the eluent to give 16 g of N-ethyloxalyl-2-(2-tetrahydropyranyloxyethyl)-3,4-dichlorobenzeneethanamine.

Step 2

16 g of the product obtained above are dissolved in 40 ml of THF and added dropwise to a suspension of 1.7 g of $LiAlH_4$ in 5 ml of THF at 50° C. The reaction mixture is refluxed for 4 hours, cooled, hydrolyzed, filtered and concentrated under vacuum. The residue is chromatographed on silica gel using $CH_2Cl_2/CH_3OH$ (100/5 v/v) as the eluent to give 14 g of N-(2-hydroxyethyl)-2-(2-tetrahydropyranyloxyethyl)-3,4-dichlorobenzeneethanamine under the form of an oil.

Step 3

3.55 g of BOP are added at 0° C. to a solution of 2.4 g of the product prepared above, 1.1 g of triethylamine and 1.3 g of 3-isopropoxyphenylacetic acid in 60 ml of $CH_2Cl_2$. The reaction mixture is stirred for one hour at 0° C. and is then successively concentrated under vacuum, taken up in AcOET, washed with water, dried over $Na_2SO_4$ and concentrated under vacuum. The residue is chromatographed on silica gel using $CH_2Cl_2/CH_3OH$ (100/3 v/v) as the eluent to give 2.2 g of N-(2-hydroxyethyl)-N-(3-isopropoxyphenylacetyl)-2-(2-tetrahydropyranyloxyethyl)-3,4-dichlorobenzeneethanamine under the form of an oil.

Step 4

0.41 g of acetyl chloride is added to a solution of 2.2 g of the product obtained above in 10 ml of $CH_2Cl_2$ in the presence of 0.56 g of triethylamine in $CH_2Cl_2$. The reaction mixture is stirred for one hour and is then successively concentrated under vacuum, washed with ethyl ether, with water, dried over $Na_2SO_4$ and concentrated under vacuum to give 2 g of N-(2-acetoxyethyl)-N-(3-isopropoxyphenylacetyl)-2-(2-tetrahydro pyranyloxyethyl)-3,4-dichlorobenzeneethanamine under the form of an oil.

Step 5

2 g of the oil obtained above are dissolved in 20 ml of methanol saturated with HCl and the mixture is stirred for one hour at room temperature. The reaction mixture is concentrated under vacuum, the residue is taken up in AcOET, washed with water, dried over $Na_2SO_4$ and chromatographed on silica gel using $CH_2Cl_2/CH_3OH$ (100/3 v/v) as the eluent to give 1.2 g of N-(2-acetoxyethyl)-N-(3-isopropoxyphenylacetyl)-2-hydroxyethyl-3,4-dichlorobenzeneethanamine under the form of an oil.

Step 6

0.5 g of the product prepared above is dissolved in 10 ml of $CH_2Cl_2$ in the presence of 0.11 g of triethylamine. 0.125 g of mesyl chloride is added and the reaction mixture is stirred for 30 minutes at room temperature. The reaction mixture is concentrated under vacuum and then the residue is successively taken up in AcOET, washed with water, dried over $Na_2SO_4$ and concentrated under vacuum to give 0.5 g of N-(2-acetoxyethyl)-N-(3-isopropoxyphenylacetyl)-2-mesyloxyethyl-3,4-dichlorobenzeneethanamine under the form of an oil.

Step 7

0.5 g of the product prepared above and 0.25 g of 4-phenylquinuclidine are dissolved in 1 ml of dimethylformamide and the reaction mixture is heated at 80° C. for two hours. The reaction mixture is poured into water and then successively extracted with AcOET, washed with water, with a saturated solution of NaCl, concentrated under vacuum and the residue is chromatographed on silica gel using $CH_2Cl_2/CH_3OH$ (100/5 v/v) as the eluent. The pure fractions are concentrated under vacuum, the residue is taken up in $CH_2Cl_2$ and precipitated by adding ethyl ether to give 0.45 g of 1-[3-(3,4-dichlorophenyl)-4-(N-(2-acetoxyethyl)-3-isopropoxyphenylacetylamino)butyl]-1-azoniabicyclo[2.2.2.]octane chloride (Compound 13). M.p.= 90°–92° C.

EXAMPLE 14

1-[3-(3,4-dichlorophenyl)-4-[N-(2-methoxyethyl)-3-isopropoxyphenylacetamido]-butyl]-4-phenyl-1-azoniabicyclo[2.2.2.]octane chloride

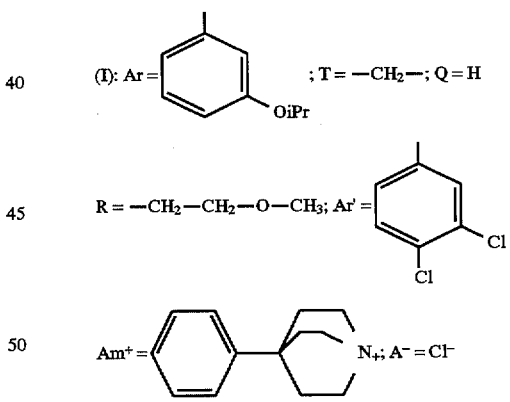

Step 1

N-methoxyacetyl-2-(3,4-dichlorophenyl)-4-(tetrahydropyran-2-yloxy)butylamine

A mixture of 8.6 g of 2-(3,4-dichlorophenyl)-4-(tetrahydropyran-2-yloxy)butylamine (obtained according to PREPARATION (I), step (b)), 2.46 g of methoxyacetic acid, 5.55 g of triethylamine in 50 ml of dichloromethane is cooled to 0° C. and 14.5 g of BOP is added thereto. The reaction mixture is stirred for one hour at room temperature and concentrated under vacuum. The residue is taken up in ethyl acetate and is successively washed with water, dried over $Na_2SO_4$ and concentrated under vacuum. The residue is chromatographed on silica gel using $CH_2Cl_2/CH_3OH$ (100/1 v/v) as the eluent to give 7.5 g of the expected product.

Step 2
N-(2-methoxyethyl)-2-(3,4-dichlorophenyl)-4-(tetrahydropyran-2-yloxy)butylamine A suspension of 1.5 g of LiAlH$_4$ in 30 ml of tetrahydrofuran (THF) is refluxed and a solution of 7.5 g of the product obtained in step 1 in 40 ml of THF are added dropwise thereto.

The reaction mixture is refluxed for 3 hours, cooled, hydrolyzed, filtered and the filtrate is concentrated under vacuum. The residue is chromatographed on silica gel using CH$_2$Cl$_2$/CH$_3$OH (100/5 v/v) as the eluent to give 4.1 g of the expected product.

Step 3
N-(3-isopropoxyphenylacetyl)-N-(2-methoxyethyl)-2-(3,4-dichlorophenyl)-4-(tetrahydropyran-2-yloxy)butylamine 2.6 g of BOP are added to a solution cooled at 0° C. of 1.9 g of the product prepared in step 2, 1.2 g of triethylamine and 0.96 g of 3-isopropoxyphenylacetic acid in 50 ml of CH$_2$Cl$_2$. The reaction mixture is stirred for one hour and is then concentrated under vacuum. The residue is taken up in ethyl acetate, washed with water, dried over Na$_2$SO$_4$ and concentrated under vacuum. 2.2 g of the expected product is obtained, which is directly used in the next step.

Step 4
N-(3-isopropoxyphenylacetyl)-N-(2-methoxyethyl)-2-(3,4-dichlorophenyl)-4-hydroxybutylamine A saturated solution of hydrochloric acid in diethylether is added to a solution of 2.2 g of the product obtained in step 3 in 30 ml of methanol, until the obtention of a pH value of 1.

The reaction mixture is stirred at ambient temperature for 30 min. and is then concentrated under vacuum. The residue is taken up with ethyl acetate, washed with water, dried over Na$_2$SO$_4$ and concentrated under vacuum to give 1.8 g of the expected product which is directly used in the next step.

Step 5
N-(3-isopropoxyphenylacetyl)-N-(2-methoxyethyl)-2-(3,4-dichlorophenyl)-4-mesyloxybutylamine 0.526 g of methanesulfonyl chloride are added to a mixture of 1.8 g of the product obtained in step 4 and 0.46 g of triethylamine in 40 ml of dichloromethane. The reaction mixture is stirred at ambient temperature for 1 h and is then concentrated under vacuum. The residue is taken up with ethyl acetate, washed with water, dried over Na$_2$SO$_4$ and concentrated under vacuum to give 2 g of the expected product.

Step 6
1-[3-(3,4-dichlorophenyl)-4-[N-(2-methoxyethyl)-3-isopropoxyphenylacetamido]-butyl]-4-phenyl-1-azoniabicyclo[2.2.2]octane chloride 2 g of the product prepared in step 5 and 1 g of 4-phenylquinuclidine are dissolved in 2 ml of dimethylformamide and the reaction mixture is heated at 80° C. for 4 hours. After cooling, the reaction mixture is poured into water and then successively extracted with ethyl acetate, washed with a 5% solution of hydrochloric acid, with a saturated solution of NaCl, dried over Na$_2$SO$_4$ and concentrated under vacuum.

The residue is chromatographed on silica gel using CH$_2$Cl$_2$/CH$_3$OH (100/1 v/v) as the eluent. 0.9 g of the expected compound are obtained. M.P.=85°–88° C.

Compounds 15 to 22 described in TABLE III below are prepared by following the methods described above.

TABLE III

Ar—T—CO—N(—CH$_2$—C(R—Q)(Ar')—CH$_2$—CH$_2$—Am$^+$A$^-$)

| Example | Ar | T | Ar' | —R—Q— | Am$^+$A$^-$ | M.p °C./NMR |
|---|---|---|---|---|---|---|
| 15 | 3-OiPr-phenyl | —CH$_2$— | 3,4-difluorophenyl | —(CH$_2$)$_3$— | 4-phenyl-1-azoniabicyclo[2.2.2]octane, Cl$^-$ | 122 |
| 16 | 3-OiPr-phenyl | —CH$_2$— | 3,4-dichlorophenyl | —(CH$_2$)$_4$— | 4-phenyl-1-azoniabicyclo[2.2.2]octane, Cl$^-$ | 115 |
| 17 | 3-OiPr-phenyl | —CH$_2$— | 3,4-dichlorophenyl | —(CH$_2$)$_3$— | 4-benzyl-1-azoniabicyclo[2.2.2]octane, Cl$^-$ | NMR (200 MHz in DMSO) 0,7–2,2:m:18 H, 2,4–4,6:m:17 H, 6,4–7,8:m:12 H $\alpha_D$=+16 (c = 1, MeOH) |

TABLE III-continued $$Ar-T-CO-\underset{\underset{}{|}}{N}-CH_2-\underset{\underset{Ar'}{|}}{\overset{R-Q}{C}}-CH_2-CH_2-Am^+A^-$$

| Example | Ar | T | Ar' | —R—Q— | Am⁺A⁻ | M.p °C./NMR |
|---------|----|----|------|--------|--------|-------------|
| 18 | 3,5-bis(CF₃)phenyl | — | 3,4-diCl-phenyl | —(CH₂)₂— | phenyl-N⁺ quinuclidine Cl⁻ | 165 |
| 19 | 3,5-bis(CF₃)phenyl | — | 3,4-diCl-phenyl | —(CH₂)₂— | benzyl-N⁺ quinuclidine Cl⁻ | 148 |
| 20 | 3-Cl-phenyl | —CH₂— | 3,4-diCl-phenyl | —(CH₂)₃— | benzyl-N⁺ quinuclidine Cl⁻ | 240 |
| 21 | 3-Cl-phenyl | —CH₂— | 3,4-diCl-phenyl | —(CH₂)₃— | phenyl-N⁺ quinuclidine Cl⁻ | 172 |
| 22 | 3-Cl-phenyl | —CH₂— | 3,4-diCl-phenyl | —(CH₂)₂— | benzyl-N⁺ quinuclidine Cl⁻ | 149 |

EXAMPLE 23

Tablet comprising:
Compound 4 250 mg
Lactose 80 mg
Crosslinked polyvidone 20 mg
Methyl hydroxypropyl cellulose 10 mg
Hydrogenated castor oil 40 mg

EXAMPLE 24

Enteric tablet comprising:
Tablet:
Compound 4 250 mg
Hydroxypropyl cellulose 6 mg
Lactose 62 mg
Microcrystalline cellulose 60 mg
Carboxymethyl starch 12 mg
Polyethylene glycol 6000 10 mg
Coating:
Endraget L 100 1 mg
Dibutyl phthalate 1 mg
Isopropyl alcohol (evaporated) 28 mg

EXAMPLE 25

Solution to be taken orally, comprising:
Compound 4 100 mg
Ethyl alcohol 100 mg
Propylene glycol 50 mg
Polyvidone excipient 20 mg
Glycerol 50 mg
Artificial flavoring 2.5 mg
Purified water qsp 1.0 mg

EXAMPLE 26

Injectable suspension containing:
Compound 4 50 mg
Polysorbate 80 1.5 mg
Polyoxyethylene glycol 20 mg
Methyl and propyl parahydroxybenzoate 1.5 mg
Sorbitol 30 mg
Polyvidone excipient 10 mg
Water for injectable preparations qsp 1 mg

EXAMPLE 27

Gelatin capsule comprising:
Compound 4 from 2.5 to 250 mg

Modified maize starch 50 mg
Talc 25 mg
Anhydrous colloidal silica 1 mg
Stearic acid 10 mg
Lactose qsp 100 mg

EXAMPLE 28

Suppository comprising:
Compound 4 150 mg
Solid semisynthetic glycerides qsp

What is claimed is:

1. A quaternary basic amide of the formula

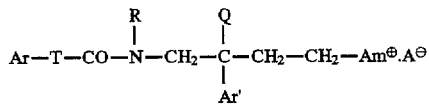
(I)

in which

Ar is a phenyl which is mono- or di-substituted by a $C_1$–$C_4$ alkoxy, a halogen or a trifluoromethyl group;

T is a direct bond, a hydroxymethylene group, an alkoxymethylene group in which the alkoxy group is $C_1$–$C_4$, or a $C_1$–$C_5$-alkylene group;

Ar' is a phenyl which is unsubstituted or mono- or poly-substituted by a substituent selected from the group consisting of a halogen atom, a trifluoromethyl, a $C_1$–$C_4$-alkoxy and a $C_1$–$C_4$-alkyl, said substituents being identical or different; a thienyl; a benzothienyl; a naphthyl; or an indolyl;

R is hydrogen, a $C_1$–$C_4$-alkyl, an ω-($C_1$–$C_4$)alkoxy($C_2$–$C_4$)alkyl, or an ω-($C_2$–$C_4$)alkanoyloxy($C_2$–$C_4$)alkyl;

Q is hydrogen;

or else Q and R together form a 1,2-ethylene, 1,3-propylene or 1,4-butylene group;

$Am^\oplus$ is selected from the group consisting of a 1-azoniabicyclo[2.2.2]octane, 4-phenyl-1-azoniabicyclo[2.2.2]octane and 4-benzyl-1-azoniabicyclo[2.2.2]octane; and $A^\ominus$ is a pharmaceutically acceptable anion.

2. A quaternary basic amide of formula (I) according to claim 1, wherein T is a direct bond or a methylene group.

3. A quaternary basic amide of formula (I) according to claim 1, wherein Q and R together form a 1,2-ethylene 1,3-propylene or 1,4-butylene group.

4. A quaternary basic amide according to claim 1 wherein Ar is selected from the group consisting of 3-isopropoxyphenyl, 3,5-difluoromethylphenyl and 3-chlorophenyl.

5. A quaternary basic amide according to claim 1 wherein Ar' is selected from the group consisting of 3,4-dichlorophenyl and 3,4-difluorophenyl.

6. A quaternary basic amide according to claim 1 wherein $A^\ominus$ is an anion selected from the group consisting of chloride, bromide, iodide, hydrogensulfate, methanesulfonate, paratoluenesulfonate and acetate.

7. A quaternary basic amide according to claim 1 wherein:
Ar is a 3-isopropoxyphenyl;
T is a methylene group;
Ar' is a 3,4-difluorophenyl or a 3,4-dichlorophenyl;
Q and R together form a 1,3-propylene group or a 1,4-butylene group; and
$Am^\oplus$ is a 4-phenyl-1-azoniabicyclo2.2.2]octane or a 4-benzyl-1-azoniabicyclo-[2.2.2]octane.

8. A quaternary basic amide according to claim 1 wherein:
Ar is a 3,5-ditrifluoromethylphenyl;
T is a direct bond;
Ar' is a 3,4-dichlorophenyl;
Q and R together form a 1,2-ethylene group; and
$Am^\oplus$ is a 4-phenyl-1-azoniabicyclo[2.2.2]octane or a 4-benzyl-1-azoniabicyclo-[2.2.2]octane.

9. A quaternary basic amide according to claim 1 wherein:
Ar is a 3-chlorophenyl;
T is a methylene group;
Ar' is a 3,4-dichlorophenyl;
Q and R together form a 1,2 ethylene group or a 1,3-propylene group; and
$Am^\oplus$ is a 4-phenyl-1-azoniabicyclo[2.2.2]octane or a 4-benzyl-1-azoniabicyclo-[2.2.2]octane.

10. A pharmaceutical composition comprising an effective amount of a compound as claimed in claim 1 and a pharmaceutically acceptable excipient.

11. A pharmaceutical composition in the form of a dosage, unit, containing an effective amount of a compound of formula (I) according to claim 1 as active principle, and at least one pharmaceutical excipient.

12. A pharmaceutical composition comprising an effective amount of a compound as claimed in claim 2 and a pharmaceutically acceptable excipient.

13. A pharmaceutical composition comprising an effective amount of a compound as claimed in claim 3 and a pharmaceutically acceptable excipient.

14. A pharmaceutical composition comprising an effective amount of a compound as claimed in claim 4 and a pharmaceutically acceptable excipient.

15. A pharmaceutical composition comprising an effective amount of a compound as claimed in claim 5 and a pharmaceutically acceptable excipient.

16. A pharmaceutical composition comprising an effective amount of a compound as claimed in claim 6 and a pharmaceutically acceptable excipient.

17. A pharmaceutical composition comprising an effective amount of a compound as claimed in claim 7 and a pharmaceutically acceptable excipient.

18. A pharmaceutical composition comprising an effective amount of a compound as claimed in claim 8 and a pharmaceutically acceptable excipient.

19. A pharmaceutical composition comprising an effective amount of a compound as claimed in claim 9 and a pharmaceutically acceptable excipient.

* * * * *